US006294712B1

(12) United States Patent
Kleine et al.

(10) Patent No.: US 6,294,712 B1
(45) Date of Patent: Sep. 25, 2001

(54) NEMATODE-RESISTANT GENE

(75) Inventors: Michael Kleine; Daguang Cai, both of Kiel; Christian Jung, Zum Aml 15, Daenischenhagen, all of (DE)

(73) Assignees: Christian Jung, Daenischenhgen (DE); Danisco Biotechnology, Kopenhagen (DK); DLO-Centrum Voor Planteneredlings, Wageningen (NL); Johannes Dieckmann, Nienstaedt (DE); K. A. Marcker, Aarhus (DK); Planta Angerwandte Pflanengenetik, Einbeck (DE)

( * ) Notice: Subject to any disclaimer, the term of this patent is extended or adjusted under 35 U.S.C. 154(b) by 0 days.

(21) Appl. No.: 09/269,040

(22) PCT Filed: Sep. 18, 1997

(86) PCT No.: PCT/EP97/05130

§ 371 Date: May 26, 1999

§ 102(e) Date: May 26, 1999

(87) PCT Pub. No.: WO98/12335

PCT Pub. Date: Mar. 26, 1998

(30) Foreign Application Priority Data

Sep. 18, 1996 (DE) ........................................ 196 37 974
Jan. 13, 1997 (DE) ........................................ 197 00 844

(51) Int. Cl.[7] ........................ C12N 5/04; C12N 15/29; C12N 15/82; A01H 5/00

(52) U.S. Cl. ........................ 800/279; 800/278; 800/298; 800/306; 800/317; 800/301; 435/69.1; 435/320.1; 435/419; 435/468; 536/23.1; 536/23.6

(58) Field of Search ................................ 800/279, 278, 800/298, 306, 317, 301; 435/320.1, 69.1, 468, 419; 536/23.1, 23.6

(56) References Cited

U.S. PATENT DOCUMENTS 5,750,386 * 5/1998 Conkling et al. ................ 435/172.3

FOREIGN PATENT DOCUMENTS

WO 92/15690 * 9/1993 (WO) .
WO 93/19181 * 9/1993 (WO) .

OTHER PUBLICATIONS

Salentija et al. Mol. Gen. Genet. vol. 235, pp. 432–440, 1992.*

Lindsey et al. Journal of Exp. Botany, vol. 41, No. 226, pp. 529–536, 1990.*

Sambrook J., et al. Molecular Cloning, A laboratory manual, 2nd edition, Cold Spring Harbor Laboratory Press, 1989.*

Lagudah et al.; "Map–Based Cloning of a Gene Sequence Encoding a Nucleotide–Binding Domain and a Leucine–Rich Region at the CRE3 Nematode Resistance Locus of Wheat"; Genome; vol. 40; 1997; pp. 659–665.

Kleine et al.; "Physical Mapping and Cloning of a Translocation in Sugar Beet (Beta Vulgaris L.) Carrying a Gene for Nematode (Heterodera Schachtii) Resistance from B. Procumbens"; Theor Appl. Genet; vol. 90; 1995; pp. 399–406.

Kleine et al.; Breeding for Nematode Resistance in Sugarbeet: A Molecular Approach; Klawer Academic Publishers; 1997; pp. 176–190.

* cited by examiner

*Primary Examiner*—David T. Fox
*Assistant Examiner*—Medina A. Ibrahim
(74) *Attorney, Agent, or Firm*—Foley & Lardner

(57) ABSTRACT

The present invention concerns a nucleic acid and, thus, the transcribed polypeptide, that induces resistance against sedentary nematodes in plants of the Solanaceae, Chenopodiaceae and/or Brassicaceae families. The nucleic acid comprises a translated region that is at least 60% homologous to the sequence of the HS1$^{pro-1}$ gene from *Beta procumbens.* Methods of making and using a nucleic sequence of the invention are described, implementing recombinant DNA technology. For instance, vectors and plants can be engineered to contain a nucleic acid according to the invention. Furthermore, test kits containing the nucleic acid and/or a vector are provided.

24 Claims, 9 Drawing Sheets

TCTAGAGCTG TCGACGCCGG CCGGCCAATT AACCCTCACT AAAGGGAACG AATTCGGATC
TTCTTTCTTG GTGCTTATTT TTGACACTAA TCCGATTCTT AGCATTAAGT TTGAAGCACA
CCTCTTGATA AACTACGTTA CTATGTATCA TGTCAATATG CTAAGAATTT GTCTTGACCT
CATCGCTATG TATAGCATCT ATACTCTAAA CCTAGTAAAA CAAATATCCC ATCCGTCCCA
TAATATGAGT CCCCTTTCTA TTTTAGGAGT CAAAATTTTA AAATTTTTGA CCAAATATTC
TTATTACTAT ATATAAAACA TATTCATGTG GGATCTTGTT AGATTCGTCT TAATATGTAT
TTCATAATAC TAACTTTTTA ATATTTTTTT TACTAATACG AAATTGAAGA TATACAATGT
CTTAAATACT ATGCAAAAGT AACAGAACCT ATATTTTTGG GTCGGAGGGA GTAATAACGT
AACCATTGAT TGACGCATAA TTTGTATATA AATATTTTCA AATTGAATCA TCTTAAATAA
TATAGTTAAT GCTTATAAAT AAGCCTAAAG ACTGTGAATA GCAAGATCGT TAAAAATAAA
TTGAAGAAAA TATTTGATAT GGATAATGAA ATTGGAAATG GCATGCTTAG CTTCTCGGGA
ATCTTATACC GCTACATCTA TAATAAAAAT TCCTCATAAA ATTTTGCCCA TTTTAACACA
CGAAATTCGT CCTTTTACGC GAGCCCTTTC CACACGTCTT TAAAATTTAA AAACCTCGTC
TTTACTCTCC CCACCTATAT ATATACACGT CCCCCCTTCT CTACTTCCCA TCTCACATAC
ACATACCCAA TCCACAAACT TCCATCTTAT CCAACTTTC? CTCACCTATC CCCTTCTTCA
ATTTTCCAAA ACTCAAAACA AAATCAAAGA AATGGTAGAT TCCAAAACAA ACAAAATGGT
ACAATCAACA CCAAACCTCA CAAAAAAATC TCCAAAAATC ACAACCAAAC GCACAATTAT
CAACACCATT AATTTCCCCA GTACCAGTAA TTTCCGGCGA ATTATCTCCG GCGTCGGAAT
CATCCTGTTC AGCTTACGAA TCGTATCTCA AATTACCGGA GCTCCGTCAA CTATGGAGTT
CAAAAGAATT CCCCGGTTGG GATAACGAAC CGATAATCAA ACCGGCTTTG CAAGCATTAG
AGATAACATT CCGGTTCATC TCACTCGTTT TATCCGACGC TAGACCGTAC ATAAACCGGC
GAGAATGGAA CCGGAAATTA GAGTCGTTAG CGAGAGATCA AGTCCGAAAC TCATCTCAGT
TCTCTGCGGA AGACGATGAG ACACGTGGAT CAGCTCCGAA TCGTTGATCT GACGTCATCG
TATGGTGAGG TGATGTCACA AACAGAAGTT CAGCGGAGGT ATGGAAGCTT GCGAATGGAG
AACATGATAC TACCGTGGTC TGTCGTAGTA GCGAATTTAG TCTCCTTCCG AGGTTAGCCA
CGTGGCAGAA GTCGGAGGAG ATTGCTTCTA GAATCTTCTA CGCGGTTGAA TCTGCTATGA
GAAGGTGTGG GTATAGTTTG GGCCTTGGTG AGCCCAATTT GGACGGAAAG CCCAATTTAG
ATTACGACGC CGTTTGTCGT CCTTCTGAGC TTCACGCGCT TAAAAAGGGC GCGTTGGATT
ATATTCAGAA TTCGGAAAAT CAGATATTGT TTACAATTCA TCAGATTTTC GAGTCGTGGA
TTTTTTCCTC GAAAAAATTG TTGGATCGAA TAAGTGAGAG GATCAGTAAA GAAGAGTTTA
CCAAAGCAGC AGATGATTGT TGGATACTGG AGAAAATATG GAAGTTATTG GAGGAAATCG
AGAATTTACA TTTATTAATG GATCCTGACG ATTTCCTGCA TCTGAAGACG CAACTGAGGA
TGAAAACAGT GGCGGATTCT GAAACTTTTT GTTTTCGATC AAAAGGACTG ATCGAGGTAA
CAAAATTAAG CAAGGATCTA CGGCACAAGG TGCCGAAGAT CCTTGGTGTA GAGGTGGACC
CTATGGGAGG ACCGGTGATA CAAGAGTCGG CAATGGAGTT GTACCGAGAA AAAAGAAGAT
ACGAGAAGAT ACATCTGTTA CAAGCGTTTC AAGGGGTGGA ATCCGCTGTT AAAGGGTTTT
TCTTTAATTA TAAACAGTTG TTGGTGATCA TGATGGGTAG TTTGGAAGCG AAAGCGAATT
TTGCTGTGAT TGGTGGTTCT ACTGAGTCTT CGGATTTGTT GGCTCAGTTG TTTTTAGAAC
CTACTTATTA TCCGAGTTTG GATGGTGCCA AGACTTTTAT TGGTGATTGT TGGGAGCATG
ATCAGGCTGT TGGTAGCGGC CTCGATTGTC GTCATCATCG GAAGAATCGG ACTGCGAAAC
AATGATGGTT TCGAAGTTAG TTTTGGATTG AGTTTGGTTT GATCTGACTC GGCTGAGTAA
TGGGCGGCGA TAGGGAGGTT ATGGAGAACG TGGGGCGGAA AGTGGGTGGC CTTGTTAGTG
AGACGTGCAA ACTTTGGTTA CTATTACATG TGATATACTT ATATTTAGTG GGAATATTGC
TTTGGTGTAT ATAGATAAAT TTTTGAATTA ATTGTTACAC TTGTATTAGT AAATTCTGTA
TCATGATGAT TATAACATGA ATTTTTTGTT GTGACTTTAA ATGAGATTTA TGCTCCTTAA
TCCTTATTTC ACTGATATTA TTTTTTTGTA GTCTGAGTAT AAGTGCGGAG TTTAATCAAG
CAAGAGAAAA TAATAGAAGG TGATTGCATA CTTGGATTGG AGATCAATAT CTAAAAGATG

FIG. 2A

GTTATGAAAC TATTGTGAAT AACGGAGTAC ATGTCCAACA CCACACACGT ATGACTGTGT
ACCTCTAATT TACAAAGAGA TTTACAAAAT CTAGATGAGT TTTGATATGA TCGACATTGT
CTCTAAATGG GAGATAAGAA TTAAATCGTG AGGCTCTTTG CGGCTAG?TC TTCCGAATAA
AATAAGAAAC AATGGTTTAC TCTAATTCA? TTTTCCAATT GGCAAAGTGG CACAAGCTTC
AATAA?T?GG CTCTTCACAA TTGAGTATAA AAGAATGGGT TAATTAC?CC GG?CTTTGAA
TAAAATTAAT CCTATTTAAT TGTTTTTGAA ATATTCTTAA AAATA?CGTT GTCTAATACT
TTCTTTAGTT GGGACCCGGT TCTGAACC?A CTTAAATTAA TGGGCTCAAT GGCCGCCTAA
TTTCCTCTTG TTATTTTTAG CCTTTTTTTT CCTTTTTTTC CCTTTAAAAT AACTATTTGT
TCTCTTGAAT ATCTTAAAAT ACGTGTCTAT C??CTTTAGT TGGACCGTCT GAACTATTAT
TATGCTATGC ACTATTCCTT TGTATTTACC TTTTTCTTTT TCCTTTAAAT ACTATTGTTC
TCATTTCAAT TATATTCTAT TTTTGTTAAA AAACGGTCTT AATTTTTACA ACAGTAAAAT
TATTGATTTT CCTTCTATAT TAAAATTTGA AAGTGAATGT ATTTCGAAAT TTAGGTATAT
GAATATTTAT ATTGTTCGAT TAATGATGAT AAAAGGATTT TACTCATTAA CCTAAACCAT
TTCTAGATAA GATAAGAGGA ACTTCCACCT AGTTAACATG TCTCACTTTC CTAGTAGACG
AATCTAAATT GCGTTGCTGG ATTTAGAACT TTGGTCAAGA TAATGGCAAA ACTTTCAAGC
ACCCGTAGAT GCATTTTCC? CGACATTTCT CATACAGCAC TAAACGTTTC AACTTCCTCT
TTTATTTTCT TGAAATTTTT TGTGGCAATG AGAAACGTTC GAAGTTGATC TTTGCGTTTC
GACGATTTGA AATAAGAAAA TGCGTATTGT CGGCAACTGA TTGTAGTAGT TGC?GTTATT
ATAATGATAG TCTTTTATAT AGAATTCATT TAATTCTAAT TCATTTGAAT CCAGTTAAGT
TGAGTTTAGT TTAGTCAGCC TAAAAGAACA AAGTAAGTCA TGGAATGGAA TGAAGATGTA
ATCAAATAGA GGAGGGGCTG ATAACAATAA TTATTACTTA TGTTGCGTGT TCAATTCAGT
AATGAAAAAA ATAAGGTTGA ATTAGGAGGG TAATACAATT ATTACCGGTG ATGTGATAAA
ACTAATGTTT AAGGGTTTAA GTTACTCTAA ACCCTCAATT AAACATAGTC TAACAAAAAA
TTCTCATAAT CTAAATCAAA CACGTACTTA TACAATCCTC TACATGAATC CGTTTCTAAC
TCTAAAGGAA GATCGATACT TATTAGAATC CGTTTCCAAC CCTAAAAATG ACTGATCAAA
GGTTCATGGA TTTTGGAAGG GAAAGACGAA TGCGAGGGCA GTGTACAGGA TAATGTGCAT
GAGATGGCAA GGGTCATGCT AGTTAGAGCA AAATATA?AT GACTTAATTC AAAAACTACC
TACTATTTCA AATTAATAGA CTTTATTGGA GTCATGAAGT GTACTGTTTG GTACACCCCA
CATTACTCAT GCACTACACC TAATTTGTCA CAGCATTCAG CTGCCCTTGT TTTGCAGTCT
TTGGAGCTGG CGTGCCTCTT GTTGCTGGTT AGTCGGCGCT TGGTCTGTTG TG??GTGACC
CTCTGTTTTT TTTTTTTTTT AAAATGGTCG CTGATTACTA T?CTGTGTAT T?CATTTTGT
ACTCCCTCGT ATCCAATTAT ATGCTACACT TTTTTTGCGG ACTCCAAAAC GTTTTTTTTT
T?TGTCCGAG AGATAGAGAG GAAAAGCCCA TGTTGTTAGG AGAGAG?TCG GGAGAAGGAA
AAGCCAAATA AAGAAGTAAT AACATCTAAA TAAGAAAATT CCTTTGATGG AAAGTGTAGC
GACTAAAAAA CGAAGGACAA TATGTAGTTT TCATATGCCT TTACCTTTGC AATCTCCTTT
TTTATTGTTT ACCCATACTG GATTAGGTTG GATTTATCAA CACAAAATGA GTTGGACTAT
ATCACTACAT TACTGTGGTC CTGTGGATAC ATCAACAAAA AAAATGAGTT GGACCATATC
AATGTGTTAG CGTGGATTAT GTACACATTG GACTGGAGTT GAAGCAAATA TAATCTGAAA
AGGGCGATGG GTTAGGTCAT GAGGTATTTA GAATAAGACT TTGATCAAGC CCAAATCCAC
CCGCAAAGAA TTATACCCTT TATTTTCAAG GCACCATCAC TGCATAAAAT AATCTGAAAT
GCCACAAAAG ATTAACGTCC AATATGCTCA CAGCCAAAAA TCAATCCATT ATTGTTTGGT
AAGAAAAGGT AATAGGCTAG ATCAATTTGC TGCCAATTGC CAGGCCTGTG GGCCTGTCAC
CTGTGGGTAA TTTAATATG? CTCTTTTGGG TCGGCCTGTT AAGTACACCA ACATGAACTT
AAAGCTT

FIG. 2B

SEQUENCE LISTING

```
<160> NUMBER OF SEQ ID NOS: 7

<210> SEQ ID NO 1
<211> LENGTH: 5401
<212> TYPE: DNA
<213> ORGANISM: Beta vulgaris
<220> FEATURE:
<221> NAME/KEY: unsure
<222> LOCATION: (2982)
<223> OTHER INFORMATION: n may be A or G or C or T/U, or the nucleotide
      is not present
<220> FEATURE:
<221> NAME/KEY: unsure
<222> LOCATION: (3024)
<223> OTHER INFORMATION: n may be A or G or C or T/U, or the nucleotide
      is not present
<220> FEATURE:
<221> NAME/KEY: unsure
<222> LOCATION: (3060)
<223> OTHER INFORMATION: n may be A or G or C or T/U, or the nucleotide
      is not present
<220> FEATURE:
<221> NAME/KEY: unsure
<222> LOCATION: (3062)
```

-continued

```
<223> OTHER INFORMATION: n may be A or G or C or T/U, or the nucleotide
      is not present
<220> FEATURE:
<221> NAME/KEY: unsure
<222> LOCATION: (3102)
<223> OTHER INFORMATION: n may be A or G or C or T/U, or the nucleotide
      is not present
<220> FEATURE:
<221> NAME/KEY: unsure
<222> LOCATION: (3107)
<223> OTHER INFORMATION: n may be A or G or C or T/U, or the nucleotide
      is not present
<220> FEATURE:
<221> NAME/KEY: unsure
<222> LOCATION: (3160)
<223> OTHER INFORMATION: n may be A or G or C or T/U, or the nucleotide
      is not present
<220> FEATURE:
<221> NAME/KEY: unsure
<222> LOCATION: (3203)
<223> OTHER INFORMATION: n may be A or G or C or T/U, or the nucleotide
      is not present
<220> FEATURE:
<221> NAME/KEY: unsure
<222> LOCATION: (3326)..(3327)
<223> OTHER INFORMATION: n may be A or G or C or T/U, or the nucleotide
      is not present
<220> FEATURE:
<221> NAME/KEY: unsure
<222> LOCATION: (3734)
<223> OTHER INFORMATION: n may be A or G or C or T/U, or the nucleotide
      is not present
<220> FEATURE:
<221> NAME/KEY: unsure
<222> LOCATION: (3888)
<223> OTHER INFORMATION: n may be A or G or C or T/U, or the nucleotide
      is not present
<220> FEATURE:
<221> NAME/KEY: unsure
<222> LOCATION: (4412)
<223> OTHER INFORMATION: n may be A or G or C or T/U, or the nucleotide
      is not present
<220> FEATURE:
<221> NAME/KEY: unsure
<222> LOCATION: (4607)..(4608)
<223> OTHER INFORMATION: n may be A or G or C or T/U, or the nucleotide
      is not present
<220> FEATURE:
<221> NAME/KEY: unsure
<222> LOCATION: (4656)
<223> OTHER INFORMATION: n may be A or G or C or T/U, or the nucleotide
      is not present
<220> FEATURE:
<221> NAME/KEY: unsure
<222> LOCATION: (4666)
<223> OTHER INFORMATION: n may be A or G or C or T/U, or the nucleotide
      is not present
<220> FEATURE:
<221> NAME/KEY: unsure
<222> LOCATION: (4736)
<223> OTHER INFORMATION: n may be A or G or C or T/U, or the nucleotide
      is not present
<220> FEATURE:
<221> NAME/KEY: unsure
<222> LOCATION: (4781)
<223> OTHER INFORMATION: n may be A or G or C or T/U, or the nucleotide
      is not present
<220> FEATURE:
<221> NAME/KEY: unsure
<222> LOCATION: (5354)
<223> OTHER INFORMATION: n may be A or G or C or T/U, or the nucleotide
      is not present

<400> SEQUENCE: 1

tctagagctg tcgacgcggc cgcggaatta accctcacta aagggaacga attcggatct     60

tctttcttgg tgcttaattt tttgacacta atccgattct tagcattaag ttgaagcaca    120
```

-continued

```
ctcttgataa actatgttac tatgtatcat tgtcaatatg ctaagaattt gtcttgacct    180
catcgctatg tataagcatc taatactttc ctaaactagt aaaaacaaat attccatccg    240
tcccataata tgagtcccct ttctatttta ggagtcaaaa ttttaaaatt tttgaccaaa    300
tattcttatt actatatata aaaacatatt catgtgggat cttgttagat tcgtcttaat    360
atgtattttc ataatatcaa ctttttatat ttttttacta atacgaaatt gaagatatac    420
aatgtcttaa agactatgca aaagtaagca gaacctatat tttgggacgg agggagtaat    480
aagtaatatt gattgacgca taatttgtat ataaatattt caaattgata ctactttaaa    540
taatatagtt aatgcttata aataagccta aagactgtga atagcaagat cgttaaaaat    600
aaaatttgaa aatatttgat atggataatg aaattggaaa tggcatgctt agcttctcgg    660
gaatcttata ccgctacatc tataataaaa attcctcata aaattttgcc cattttaaca    720
cacgaaattc gtccttttac gcgagccctt tccacacgtc tttaaaattt aaaaacctcg    780
tctttactct ccccacctat atatatacac gtcccccctt ctctacttcc catctcacat    840
acacataccc aatccacaaa cttccatctt atccaacttt ctctcaccta tctccttctt    900
caattttcaa aactcaaaag aaaatggtag atttcgattg caaaacaaaa atggtacaat    960
caacaccaaa cctcacaaaa aaatctccaa aaatcacaac caaacgcaca atatcaacac   1020
cattaatttc accagtacca gtaatttccg gcgaattatc tccggcgtcg gaatcatcct   1080
gttcagctta cgaatcgtat ctcaaattac cggagctccg tcaactatgg agttcaaaag   1140
aattccccgg ttgggataac gaaccgataa tcaaaccggc tttgcaagca ttagagataa   1200
cattccggtt catctcactc gttttatccg acgctagacc gtacataaac cggcgagaat   1260
ggaaccggaa attagagtcg ttagcgagag atcaagtccg aaactcatct cagttctctg   1320
cggaagacga tgagacacgt ggatcagctc cgaatcgttg atctgacgtc atcgtatggt   1380
gaggtgatgt cacaaacaga agttcagcgg aggtatggaa gcttgcgaat ggagaacatg   1440
atactaccgt ggtctgtcgt agtagcgaat ttagtctcct tccgaggtta gccacgtggc   1500
agaagtcgga ggagattgct tctagaatct tctacgcggt tgaatctgct atgagaaggt   1560
gtgggtatag tttgggcctt ggtgagccca atttggacgg aaagcccaat ttagattacg   1620
acgccgtttg tcgtccttct gagcttcacg cgcttaaaaa gggcgcgttg gattatattc   1680
agaattcgga aaatcagata ttgtttacaa ttcatcagat tttcgagtcg tggatttttt   1740
cctcgaaaaa attgttggat cgaataagtg agaggatcag taaagaagag tttaccaaag   1800
cagcagatga ttgttggata ctggagaaaa tatggaagtt attggaggaa atcgagaatt   1860
tacatttatt aatggatcct gacgatttcc tgcatctgaa gacgcaactg aggatgaaaa   1920
cagtggcgga ttctgaaact ttttgttttc gatcaaaagg actgatcgag gtaacaaaat   1980
taagcaagga tctacggcac aaggtgccga agatccttgg tgtagaggtg gaccctatgg   2040
gaggaccggt gatacaagag tcggcaatgg agttgtaccg agaaaaaaga agatacgaga   2100
agatacatct gttacaagcg tttcaagggg tggaatccgc tgttaaaggg tttttcttta   2160
attataaaca gttgttggtg atcatgatgg gtagtttgga agcgaaagcg aattttgctg   2220
tgattggtgg ttctactgag tcttcggatt tgttggctca gttgttttta gaacctactt   2280
attatccgag tttggatggt gccaagactt ttattggtga ttgttgggag catgatcagg   2340
ctgttggtag cggcctcgat tgtcgtcatc atcggaagaa tcggactgcg aaacaatgat   2400
ggtttcgaag ttagttttgg attgagtttg gtttgatctg actcggctga gtaatgggcg   2460
gcgataggga ggttatggag aacgtggggc ggaaagtggg tggccttgtt agtgagacgt   2520
```

-continued

```
gcaaactttg gttactatta catgtgatat acttatattt agtgggaata ttgctttggt   2580
gtatatagat aaatttttga attaattgtt acacttgtat tagtaaattc tgtatcatga   2640
tgattataac atgaattttt tgttgtgact ttaaatgaga tttatgctcc ttaatcctta   2700
tttcactgat attatttttt tgtagtctga gtataagtgc ggagtttaat caagcaagag   2760
aaaataatag aaggtgattg catacttgga ttggagatca atatctaaaa gatggttatg   2820
aaactattgt gaataacgga gtacatgtcc aacaccacac acgtatgact gtgtacctct   2880
aatttacaaa gagatttaca aaatctagat gagttttgat atgatcgaca ttgtctctaa   2940
atgggagata agaattaaat cgtgaggctc tttgcggcta gntcttccga ataaaataag   3000
aaacaatggt ttactctaat tcanttttcc aattggcaaa gtggcacaag cttcaataan   3060
tnggctcttc acaattgagt ataaaagaat gggttaatta cnccggnctt tgaataaaat   3120
taatcctatt taattgtttt tgaaatattc ttaaaaatan cgttgtctaa tactttcttt   3180
agttgggacc cggttctgaa ccnacttaaa ttaatgggct caatggccgc ctaatttcct   3240
cttgttattt ttagcctttt ttttcctttt tttcccttta aaataactat ttgttctctt   3300
gaatatctta aaatacgtgt ctatcnnctt tagttggacc gtctgaacta ttattatgct   3360
atgcactatt cctttgtatt tacctttttc tttttccttt aaatactatt gttctcattt   3420
caattatatt ctatttttgt taaaaaacgg tcttaatttt tacaacagta aaattattga   3480
ttttccttct atattaaaat ttgaaagtga atgtatttcg aaatttaggt atatgaatat   3540
ttatattgtt cgattaatga tgataaaagg attttactca ttaacctaaa ccatttctag   3600
ataagataag aggaacttcc acctagttaa catgtctcac tttcctagta gacgaatcta   3660
aattgcgttg ctggatttag aactttggtc aagataatgg caaaactttc aagcacccgt   3720
agatgcattt tccncgacat ttctcataca gcactaaacg tttcaacttc ctcttttatt   3780
ttcttgaaat tttttgtggc aatgagaaac gttcgaagtt gatctttgcg tttcgacgat   3840
ttgaaataag aaaatgcgta ttgtcggcaa ctgattgtag tagttgcngt tattataatg   3900
atagtctttt atatagaatt catttaattc taattcattt gaatccagtt aagttgagtt   3960
tagtttagtc agcctaaaag aacaaagtaa gtcatggaat ggaatgaaga tgtaatcaaa   4020
tagaggaggg gctgataaca ataattatta cttatgttgc gtgttcaatt cagtaatgaa   4080
aaaaataagg ttgaattagg agggtaatac aattattacc ggtgatgtga taaaactaat   4140
gtttaagggt ttaagttact ctaaaccctc aattaaacat agtctaacaa aaaattctca   4200
taatctaaat caaacacgta cttatacaat cctctacatg aatccgtttc taactctaaa   4260
ggaagatcga tacttattag aatccgtttc caaccctaaa aatgactgat caaaggttca   4320
tggattttgg aagggaaaga cgaatgcgag ggcagtgtac aggataatgt gcatgagatg   4380
gcaagggtca tgctagttag agcaaaatat anatgactta attcaaaaac tacctactat   4440
ttcaaattaa tagactttat tggagtcatg aagtgtactg tttggtacac cccacattac   4500
tcatgcacta cacctaattt gtcacagcat tcagctgccc ttgttttgca gtctttggag   4560
ctggcgtgcc tcttgttgct ggttagtcgg cgcttggtct gttgtgnngt gaccctctgt   4620
tttttttttt ttttaaaatg gtcgctgatt actatnctgt gtattncatt ttgtactccc   4680
tcgtatccaa ttatatgcta cacttttttt gcggactcca aaacgttttt tttttntgtc   4740
cgagagatag agaggaaaag cccatgttgt taggagagag ntcgggagaa ggaaaagcca   4800
aataaagaag taataacatc taaataagaa aattcctttg atggaaagtg tagcgactaa   4860
```

-continued

```
aaaacgaagg acaatatgta gttttcatat gcctttacct ttgcaatctc ctttttttatt   4920

gtttacccat actggattag gttggattta tcaacacaaa atgagttgga ctatatcact   4980

acattactgt ggtcctgtgg atacatcaac aaaaaaaatg agttggacca tatcaatgtg   5040

ttagcgtgga ttatgtacac attggactgg agttgaagca aatataatct gaaaagggcg   5100

atgggttagg tcatgaggta tttagaataa gactttgatc aagcccaaat ccacccgcaa   5160

agaattatac cctttatttt caaggcacca tcactgcata aaataatctg aaatgccaca   5220

aaagattaac gtccaatatg ctcacagcca aaaatcaatc cattattgtt tggtaagaaa   5280

aggtaatagg ctagatcaat ttgctgccaa ttgccaggcc tgtgggcctg tcacctgtgg   5340

gtaatttaat atgnctcaaa tgggtcggcc tgttaagtac accaacatga acttaaagct   5400

t                                                                   5401
```

<210> SEQ ID NO 2
<211> LENGTH: 849
<212> TYPE: DNA
<213> ORGANISM: Artificial Sequence
<220> FEATURE:
<223> OTHER INFORMATION: Description of Artificial Sequence: nucleic acid that induces a resistance against sedentary nematodes in plants

<400> SEQUENCE: 2

```
atgagaaggt gtgggtatag tttgggcctt ggtgagccca atttggacgg aaagcccaat     60

ttagattacg acgccgtttg tcgtccttct gagcttcacg cgcttaaaaa gggcgcgttg    120

gattatattc agaattcgga aaatcagata ttgtttacaa ttcatcagat tttcgagtcg    180

tggatttttt cctcgaaaaa attgttggat cgaataagtg agaggatcag taaagaagag    240

tttaccaaag cagcagatga ttgttggata ctggagaaaa tatggaagtt attggaggaa    300

atcgagaatt tacatttatt aatggatcct gacgatttcc tgcatctgaa gacgcaactg    360

aggatgaaaa cagtggcgga ttctgaaact ttttgttttc gatcaaaagg actgatcgag    420

gtaacaaaat taagcaagga tctacggcac aaggtgccga agatccttgg tgtagaggtg    480

gaccctatgg gaggaccggt gatacaagag tcggcaatgg agttgtaccg agaaaaaaga    540

agatacgaga agatacatct gttacaagcg tttcaagggg tggaatccgc tgttaaaggg    600

tttttcttta attataaaca gttgttggtg atcatgatgg gtagtttgga agcgaaagcg    660

aattttgctg tgattggtgg ttctactgag tcttcggatt tgttggctca gttgttttta    720

gaacctactt attatccgag tttggatggt gccaagactt ttattggtga ttgttgggag    780

catgatcagg ctgttggtag cggcctcgat tgtcgtcatc atcggaagaa tcggactgcg    840

aaacaatga                                                            849
```

<210> SEQ ID NO 3
<211> LENGTH: 1774
<212> TYPE: DNA
<213> ORGANISM: Beta vulgaris

<400> SEQUENCE: 3

```
ccacaaactt ccatcttatc caactttctc tcacctatct ccttcttcaa ttttcaaaac     60

tcaaaagaaa atggtagatt tcgattgcaa aacaaaaatg gtacaatcaa caccaaacct    120

cacaaaaaaa tctccaaaaa tcacaaccaa acgcacaata tcaacaccat taatttcacc    180

agtaccagta atttccggcg aattatctcc ggcgtctgaa tcatcctgtt cagcttacga    240

atcgtatctc aaattaccgg agctccgtca actatggagt tcaaaagaat tccccggttg    300
```

-continued

```
ggataacgaa ccgataatca aaccggcttt gcaagcatta gagataacat tccggttcat    360

ctcactcgtt ttatccgacg ctagaccgta cataaaccgg cgagaatgga accggaaatt    420

agagtcgtta gcgagagatc aagtcgaact catctcagtt ctctgcgaag acgatgagac    480

acgtggatca gctccgatcg ttgatctgac gtcatcgtat ggtgaggtga tgtcacaaac    540

aggaagttca gcggaggtat ggaagcttgc gaatggagaa catgatacta ccgtggtctg    600

tcgtagtagc gaatttagtc tccttccgag gttagccacg tggcagaagt cggaggagat    660

tgcttctaga atcttctacg cggttgaatc tgctatgaga aggtgtgggt atagtttggg    720

ccttggtgag cccaatttgg acggaaagcc caatttagat tacgacgccg tttgtcgtcc    780

ttctgagctt cacgcgctta aaaagggcgc gttggattat attcagaatt cggaaaatca    840

gatattgttt acaattcatc agattttcga gtcgtggatt ttttcctcga aaaaattgtt    900

ggatcgaata agtgagagga tcagtaaaga agagtttacc aaagcagcag atgattgttg    960

gatactggag aaaatatgga agttattgga ggaaatcgag aatttacatt tattaatgga   1020

tcctgacgat ttcctgcatc tgaagacgca actgaggatg aaaacagtgg cggattctga   1080

aactttttgt tttcgatcaa aaggactgat cgaggtaaca aaattaagca aggatctacg   1140

gcacaaggtg ccgaagatcc ttggtgtaga ggtggaccct atgggaggac cggtgataca   1200

agagtcggca atggagttgt accgagaaaa aagaagatac gagaagatac atctgttaca   1260

agcgtttcaa ggggtggaat ccgctgttaa agggtttttc tttaattata aacagttgtt   1320

ggtgatcatg atgggtagtt tggaagcgaa agcgaatttt gctgtgattg gtggttctac   1380

tgagtcttcg gatttgttgg ctcagttgtt tttagaacct acttattatc cgagtttgga   1440

tggtgccaag acttttattg gtgattgttg ggagcatgat caggctgttg gtagcggcct   1500

cgattgtcgt catcatcgga agaatcggac tgcgaaacaa tgatggtttc gaagttagtt   1560

ttggattgag tttggtttga tctgactcgg ctgagtaatg ggcggcgata gggaggttat   1620

ggagaacgtg gggcggaaag tgggtggcct tgttagtgag acgtgcaaac tttggttact   1680

attacatgtg atatacttat atttagtggg aatattgctt tgtgtatata gataaatttt   1740

tgaattaatt gttacacttg tattagtaaa ttct                                1774
```

```
<210> SEQ ID NO 4
<211> LENGTH: 1705
<212> TYPE: DNA
<213> ORGANISM: Beta vulgaris

<400> SEQUENCE: 4
```

```
acaaaccaca aaattacatc ttatccaatt ttctctctcc tactatttat ctctcttcat     60

cttcaaattc aaaactcaaa atttccaaaa aacatatcag aaattcaaaa aaatggttga    120

tttcgattgc aaaacaaaaa tggttcaatc aacaccaaat ctcacaaaaa aaaaccccaa    180

aacgcatcac ttcaacgccg gtaatttcac cggtaccggt aatcgccggt gaattatcac    240

cggcatcgga atcttcatgt ttagcatacg aatcatatct ccggttaccg gagctccgag    300

aattatggag ttcaaaagaa tttccagggt ggaaaaacga gtcaataatt aaaccggctt    360

tacaagcttt agaaataact ttccggttta tttcaattat tttatccgac gctagaccgt    420

acgtgaaccg gcgtgaatgg aatcgtcgat tggagtcgtt aactcgagat caagtcgagt    480

taatctcgat attatgtgaa gatgatgaaa catctggttc tgctcccata atggatctga    540

catcatcttt cggtgaagtg atgtcacaaa ctggaagttt tacaacagaa gtatggaaac    600
```

-continued

```
atgaaactac ttcggtagta tgtcgtagta gtgaatttag tctacttcct agacttgcca    660

cgtggcataa atcagatgag atttcttcta gaatattcta cgcggttgag agcgcgatga    720

agaggtgtcc atatagtttg ggcttaggtg agcccaattt agatggaaag cccaatttgg    780

attacgacgt cgtttgtcgt cctactgaaa tccacgcgct taaaaaaggc gcgttggatt    840

atattcaaaa tccggaaaac cagattttat tcacaattca tcagattttc gagtcgtggg    900

ttttttgcgc gaaacaattg ttgattcgtg taggagagag aatcaacaaa gaagaattca    960

acaaagttgc agatgattgt tgggttttaa caagaatctg gaacattcta gaagaaatcg   1020

agaatttaca tttattaatg gatccagatg attttctaca tttgaaaact caattacgga   1080

tgaaaacgac gtcggattct gaaacatttt gtttcagatc aagaggttta attgaaatta   1140

caaaattaag taaagattta cgtcacaaag ttccagaaat tctagccgtt gaagtggacc   1200

ccatgggtgg accagtaata caagaatcag caatggagtt atatagagag aagagaaagt   1260

tcgagaagat tcatgttttg caagcatttc aaggtgttga atctgctgtg aaaggttttt   1320

tttataatta taaacaattg ttggtgatta tgatgggaag tttagaagct aaggctaatt   1380

ttgctgtaat tggtggtggt tctgaatcgt ctgatttatt ggctcagatc tttctagaac   1440

ctacttatta tcctagctta gatggtgcca agacttttat tggtgatttt tgggatcatg   1500

atcagacggt tgtgagtggg tgtgatagga aaaatcgggt tgcgaaaaat tgatcattga   1560

taaaagggcg aaagtatact tggccgtcct ccttaaccaa gtctggtttc gctcctgggt   1620

gatggtggtg gtgtcgttgg tgagacgtgg gttactttga ttacttgtta caatgtgatg   1680

atatatttag tggaatacta ttgct                                         1705
```

<210> SEQ ID NO 5
<211> LENGTH: 1490
<212> TYPE: DNA
<213> ORGANISM: Arabidopsis thaliana

<400> SEQUENCE: 5

```
acaaacacaa acacacacac caaaaaaaac acagacctta aaaaaataaa aatggttgat     60

atggattgga agaggaagat ggtatcatca gatttaccaa actcacctaa gctttcttca    120

aagcttcacg taactattcc atcaccgttc aaaatcgtcc ctgtttcatc tccgatctca    180

tgttcagcac ctgctctttg ctctgcttac gagctttacc ttcgtctccc tgagctaaga    240

aagctctggt catctcgtga ttttcctcaa tggacatcag agccgattct caaaccagct    300

cttcaagctt tggagatcag tttcagatta gttttcgccg tttgttctga tactagaccg    360

tacatcaacc accgtgaatg gaaccggagg ctagattctc tcatcacgaa gcagatccag    420

cttgtagcag cgatctgcga agatgaagaa gaagaaggta tatcagcgga ggctccggtc    480

ggcggtggac ggagttcgtt gagtttgtta ccgcagctag ctacgtggag gagatcagag    540

gctttgggga agaagatctt atatacgatc gataacgaga tgagtcggtg taagtacacg    600

ctcggactcg gtgaacaaaa catcgccgga aaaccaaatc tccggtacga tgcgatttgc    660

cgaccaaacg agatctatag cctcaaggat aatccatacg cagatcatat cgataatcac    720

gagaatcaaa ctctctatat cattcaccag atcctcgaat cgtggatcta cgcatctgga    780

aatcttctga atcgaatcgt ctcaagtatc gaagaagaga aattcggaaa agcttcaaac    840

gatgtttact tgctggagaa gatctggaaa attttagcgg agattgaaga tcttcatatg    900

ttgatggatc cggaagattt tttgaaattg aagaaacagt tacagatcaa atcgacgggt    960

aaaaacgatg cgttttgttt cagatctaaa ggattagtgg agatgatgaa gatgtcgaaa   1020
```

-continued

```
gatctgagac agaaagtacc ggcggtcttg gcggttgagg tagatccaac cggaggacca   1080

agattacaag aggcggcgat gaagctttac gcgaggaaga cagagtgcga taagattcat   1140

ttgcttcagg ggatgcaagc ggtggaagcg gcggcgaaga gtttcttctt tgggtatagg   1200

cagttagtgg cggctatgat gggaagtgcg gagatgaacg cgacggcgag tcaagagtcg   1260

tgtgactcac tgagtcagat atttatggag ccgacgtatt tcccgagcct tgacgcggca   1320

aagacgtttc tgggagagtt ttggagtcat ttgggatgat taaattttaa tttctgctgg   1380

tataattatt taatataaat ttaaattggt ggtttggttt aatttagttt gtaagatagt   1440

gaaatttttg gaacatttga cgatccatat ttgaatacaa attcattttt              1490
```

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: consensus motif
<220> FEATURE:
<221> NAME/KEY: VARIANT
<222> LOCATION: (1)
<223> OTHER INFORMATION: Xaa is any amino acid
<220> FEATURE:
<221> NAME/KEY: VARIANT
<222> LOCATION: (2)
<223> OTHER INFORMATION: Xaa is leucine or isoleucine
<220> FEATURE:
<221> NAME/KEY: VARIANT
<222> LOCATION: (3)..(4)
<223> OTHER INFORMATION: Xaa is any amino acid
<220> FEATURE:
<221> NAME/KEY: VARIANT
<222> LOCATION: (5)
<223> OTHER INFORMATION: Xaa is an aliphatic or aromatic amino acid
<220> FEATURE:
<221> NAME/KEY: VARIANT
<222> LOCATION: (6)..(7)
<223> OTHER INFORMATION: Xaa is any amino acid
<220> FEATURE:
<221> NAME/KEY: VARIANT
<222> LOCATION: (8)
<223> OTHER INFORMATION: Xaa is an aliphatic or aromatic amino acid
<220> FEATURE:
<221> NAME/KEY: VARIANT
<222> LOCATION: (9)
<223> OTHER INFORMATION: Xaa is any amino acid
<220> FEATURE:
<221> NAME/KEY: VARIANT
<222> LOCATION: (10)
<223> OTHER INFORMATION: Xaa is leucine or isoleucine
<220> FEATURE:
<221> NAME/KEY: VARIANT
<222> LOCATION: (11)..(12)
<223> OTHER INFORMATION: Xaa is any amino acid
<220> FEATURE:
<221> NAME/KEY: VARIANT
<222> LOCATION: (13)
<223> OTHER INFORMATION: Xaa is leucine or isoleucine
<220> FEATURE:
<221> NAME/KEY: VARIANT
<222> LOCATION: (14)..(15)
<223> OTHER INFORMATION: Xaa is any amino acid
<220> FEATURE:
<221> NAME/KEY: VARIANT
<222> LOCATION: (16)
<223> OTHER INFORMATION: Xaa is an aliphatic or aromatic amino acid
<220> FEATURE:
<221> NAME/KEY: VARIANT
<222> LOCATION: (17)..(19)
<223> OTHER INFORMATION: Xaa is any amino acid
<220> FEATURE:
<221> NAME/KEY: VARIANT -continued

```
<222> LOCATION: (20)
<223> OTHER INFORMATION: Xaa is leucine or isoleucine

<400> SEQUENCE: 6

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa
             20


<210> SEQ ID NO 7
<211> LENGTH: 5407
<212> TYPE: DNA
<213> ORGANISM: Beta vulgaris
<220> FEATURE:
<221> NAME/KEY: unsure
<222> LOCATION: (880)
<223> OTHER INFORMATION: n may be A or G or C or T/U, or the nucleotide
      is not present
<220> FEATURE:
<221> NAME/KEY: unsure
<222> LOCATION: (2988)
<223> OTHER INFORMATION: n may be A or G or C or T/U, or the nucleotide
      is not present
<220> FEATURE:
<221> NAME/KEY: unsure
<222> LOCATION: (3030)
<223> OTHER INFORMATION: n may be A or G or C or T/U, or the nucleotide
      is not present
<220> FEATURE:
<221> NAME/KEY: unsure
<222> LOCATION: (3066)
<223> OTHER INFORMATION: n may be A or G or C or T/U, or the nucleotide
      is not present
<220> FEATURE:
<221> NAME/KEY: unsure
<222> LOCATION: (3068)
<223> OTHER INFORMATION: n may be A or G or C or T/U, or the nucleotide
      is not present
<220> FEATURE:
<221> NAME/KEY: unsure
<222> LOCATION: (3108)
<223> OTHER INFORMATION: n may be A or G or C or T/U, or the nucleotide
      is not present
<220> FEATURE:
<221> NAME/KEY: unsure
<222> LOCATION: (3113)
<223> OTHER INFORMATION: n may be A or G or C or T/U, or the nucleotide
      is not present
<220> FEATURE:
<221> NAME/KEY: unsure
<222> LOCATION: (3166)
<223> OTHER INFORMATION: n may be A or G or C or T/U, or the nucleotide
      is not present
<220> FEATURE:
<221> NAME/KEY: unsure
<222> LOCATION: (3209)
<223> OTHER INFORMATION: n may be A or G or C or T/U, or the nucleotide
      is not present
<220> FEATURE:
<221> NAME/KEY: unsure
<222> LOCATION: (3332)..(3333)
<223> OTHER INFORMATION: n may be A or G or C or T/U, or the nucleotide
      is not present
<220> FEATURE:
<221> NAME/KEY: unsure
<222> LOCATION: (3740)
<223> OTHER INFORMATION: n may be A or G or C or T/U, or the nucleotide
      is not present
<220> FEATURE:
<221> NAME/KEY: unsure
<222> LOCATION: (3894)
<223> OTHER INFORMATION: n may be A or G or C or T/U, or the nucleotide
      is not present
<220> FEATURE:
<221> NAME/KEY: unsure
<222> LOCATION: (4418)
```

-continued

<223> OTHER INFORMATION: n may be A or G or C or T/U, or the nucleotide
      is not present
<220> FEATURE:
<221> NAME/KEY: unsure
<222> LOCATION: (4613)..(4614)
<223> OTHER INFORMATION: n may be A or G or C or T/U, or the nucleotide
      is not present
<220> FEATURE:
<221> NAME/KEY: unsure
<222> LOCATION: (4662)
<223> OTHER INFORMATION: n may be A or G or C or T/U, or the nucleotide
      is not present
<220> FEATURE:
<221> NAME/KEY: unsure
<222> LOCATION: (4672)
<223> OTHER INFORMATION: n may be A or G or C or T/U, or the nucleotide
      is not present
<220> FEATURE:
<221> NAME/KEY: unsure
<222> LOCATION: (4742)
<223> OTHER INFORMATION: n may be A or G or C or T/U, or the nucleotide
      is not present
<220> FEATURE:
<221> NAME/KEY: unsure
<222> LOCATION: (4787)
<223> OTHER INFORMATION: n may be A or G or C or T/U, or the nucleotide
      is not present
<220> FEATURE:
<221> NAME/KEY: unsure
<222> LOCATION: (5360)
<223> OTHER INFORMATION: n may be A or G or C or T/U, or the nucleotide
      is not present

<400> SEQUENCE: 7

```
tctagagctg tcgacgccgg ccggccaatt aaccctcact aaagggaacg aattcggatc     60
ttctttcttg gtgcttattt ttgacactaa tccgattctt agcattaagt ttgaagcaca    120
cctcttgata aactacgtta ctatgtatca tgtcaatatg ctaagaattt gtcttgacct    180
catcgctatg tatagcatct atactctaaa cctagtaaaa caaatatccc atccgtccca    240
taatatgagt cccctttcta ttttaggagt caaaatttta aaatttttga ccaaatattc    300
ttattactat atataaaaca tattcatgtg ggatcttgtt agattcgtct taatatgtat    360
ttcataatac taacttttta atattttttt tactaatacg aaattgaaga tatacaatgt    420
cttaaatact atgcaaaagt aacagaacct atatttttgg gtcggaggga gtaataacgt    480
aaccattgat tgacgcataa tttgtatata aatattttca aattgaatca tcttaaataa    540
tatagttaat gcttataaat aagcctaaag actgtgaata gcaagatcgt taaaaataaa    600
ttgaagaaaa tatttgatat ggataatgaa attggaaatg gcatgcttag cttctcggga    660
atcttatacc gctacatcta taataaaaat tcctcataaa atttgcccca ttttaacaca    720
cgaaattcgt ccttttacgc gagccctttc cacacgtctt taaaatttaa aaacctcgtc    780
tttactctcc ccacctatat atatacacgt ccccccttct ctacttccca tctcacatac    840
acatacccaa tccacaaact tccatcttat ccaactttcn ctcacctatc cccttcttca    900
attttccaaa actcaaaaca aaatcaaaga aatggtagat tccaaaacaa acaaaaatggt   960
acaatcaaca ccaaacctca caaaaaaatc tccaaaaatc acaaccaaac gcacaattat   1020
caacaccatt aatttcccca gtaccagtaa tttccggcga attatctccg gcgtcggaat   1080
catcctgttc agcttacgaa tcgtatctca aattaccgga gctccgtcaa ctatggagtt   1140
caaaagaatt ccccggttgg gataacgaac cgataatcaa accggctttg caagcattag   1200
agataacatt ccggttcatc tcactcgttt tatccgacgc tagaccgtac ataaaccggc   1260
gagaatggaa ccggaaatta gagtcgttag cgagagatca agtccgaaac tcatctcagt   1320
```

-continued

```
tctctgcgga agacgatgag acacgtggat cagctccgaa tcgttgatct gacgtcatcg   1380
tatggtgagg tgatgtcaca aacagaagtt cagcggaggt atggaagctt gcgaatggag   1440
aacatgatac taccgtggtc tgtcgtagta gcgaatttag tctccttccg aggttagcca   1500
cgtggcagaa gtcggaggag attgcttcta gaatcttcta cgcggttgaa tctgctatga   1560
gaaggtgtgg gtatagtttg ggccttggtg agcccaattt ggacggaaag cccaatttag   1620
attacgacgc cgtttgtcgt ccttctgagc ttcacgcgct taaaaagggc gcgttggatt   1680
atattcagaa ttcggaaaat cagatattgt ttacaattca tcagattttc gagtcgtgga   1740
ttttttcctc gaaaaaattg ttggatcgaa taagtgagag gatcagtaaa gaagagttta   1800
ccaaagcagc agatgattgt tggatactgg agaaaatatg gaagttattg gaggaaatcg   1860
agaatttaca tttattaatg gatcctgacg atttcctgca tctgaagacg caactgagga   1920
tgaaaacagt ggcggattct gaaacttttt gttttcgatc aaaaggactg atcgaggtaa   1980
caaaattaag caaggatcta cggcacaagg tgccgaagat ccttggtgta gaggtggacc   2040
ctatgggagg accggtgata caagagtcgg caatggagtt gtaccgagaa aaaagaagat   2100
acgagaagat acatctgtta caagcgtttc aaggggtgga atccgctgtt aaagggtttt   2160
tctttaatta taaacagttg ttggtgatca tgatgggtag tttggaagcg aaagcgaatt   2220
ttgctgtgat tggtggttct actgagtctt cggatttgtt ggctcagttg tttttagaac   2280
ctacttatta tccgagtttg gatggtgcca agacttttat tggtgattgt tgggagcatg   2340
atcaggctgt tggtagcggc ctcgattgtc gtcatcatcg gaagaatcgg actgcgaaac   2400
aatgatggtt tcgaagttag ttttggattg agtttggttt gatctgactc ggctgagtaa   2460
tgggcggcga tagggaggtt atggagaacg tggggcggaa agtgggtggc cttgttagtg   2520
agacgtgcaa actttggtta ctattacatg tgatatactt atatttagtg ggaatattgc   2580
tttggtgtat atagataaat ttttgaatta attgttacac ttgtattagt aaattctgta   2640
tcatgatgat tataacatga attttttgtt gtgactttaa atgagattta tgctccttaa   2700
tccttatttc actgatatta tttttttgta gtctgagtat aagtgcggag tttaatcaag   2760
caagagaaaa taatagaagg tgattgcata cttggattgg agatcaatat ctaaaagatg   2820
gttatgaaac tattgtgaat aacggagtac atgtccaaca ccacacacgt atgactgtgt   2880
acctctaatt tacaaagaga tttacaaaat ctagatgagt tttgatatga tcgacattgt   2940
ctctaaatgg gagataagaa ttaaatcgtg aggctctttg cggctagntc ttccgaataa   3000
aataagaaac aatggtttac tctaattcan ttttccaatt ggcaaagtgg cacaagcttc   3060
aataantngg ctcttcacaa ttgagtataa aagaatgggt taattacncc ggnctttgaa   3120
taaaattaat cctatttaat tgtttttgaa atattcttaa aaatancgtt gtctaatact   3180
ttctttagtt gggacccggt tctgaaccna cttaaattaa tgggctcaat ggccgcctaa   3240
tttcctcttg ttatttttag cctttttttt cctttttttc cctttaaaat aactatttgt   3300
tctcttgaat atcttaaaat acgtgtctat cnnctttagt tggaccgtct gaactattat   3360
tatgctatgc actattcctt tgtatttacc tttttctttt tcctttaaat actattgttc   3420
tcatttcaat tatattctat ttttgttaaa aaacggtctt aatttttaca acagtaaaat   3480
tattgatttt ccttctatat taaaatttga aagtgaatgt atttcgaaat ttaggtatat   3540
gaatatttat attgttcgat taatgatgat aaaaggattt tactcattaa cctaaaccat   3600
ttctagataa gataagagga acttccacct agttaacatg tctcactttc ctagtagacg   3660
aatctaaatt gcgttgctgg atttagaact ttggtcaaga taatggcaaa actttcaagc   3720
```

-continued

```
acccgtagat gcattttccn cgacatttct catacagcac taaacgtttc aacttcctct   3780
tttattttct tgaaattttt tgtggcaatg agaaacgttc gaagttgatc tttgcgtttc   3840
gacgatttga aataagaaaa tgcgtattgt cggcaactga ttgtagtagt tgcngttatt   3900
ataatgatag tcttttatat agaattcatt taattctaat tcatttgaat ccagttaagt   3960
tgagtttagt ttagtcagcc taaaagaaca aagtaagtca tggaatggaa tgaagatgta   4020
atcaaataga ggaggggctg ataacaataa ttattactta tgttgcgtgt tcaattcagt   4080
aatgaaaaaa ataaggttga attaggaggg taatacaatt attaccggtg atgtgataaa   4140
actaatgttt aagggtttaa gttactctaa accctcaatt aaacatagtc taacaaaaaa   4200
ttctcataat ctaaatcaaa cacgtactta tacaatcctc tacatgaatc cgtttctaac   4260
tctaaaggaa gatcgatact tattagaatc cgtttccaac cctaaaaatg actgatcaaa   4320
ggttcatgga ttttggaagg gaaagacgaa tgcgagggca gtgtacagga taatgtgcat   4380
gagatggcaa gggtcatgct agttagagca aaatatanat gacttaattc aaaaactacc   4440
tactatttca aattaataga ctttattgga gtcatgaagt gtactgtttg gtacacccca   4500
cattactcat gcactacacc taatttgtca cagcattcag ctgcccttgt tttgcagtct   4560
ttggagctgg cgtgcctctt gttgctggtt agtcggcgct tggtctgttg tgnngtgacc   4620
ctctgttttt tttttttttt aaaatggtcg ctgattacta tnctgtgtat tncattttgt   4680
actccctcgt atccaattat atgctacact ttttttgcgg actccaaaac gttttttttt   4740
tntgtccgag agatagagag gaaaagccca tgttgttagg agagagntcg ggagaaggaa   4800
aagccaaata aagaagtaat aacatctaaa taagaaaatt cctttgatgg aaagtgtagc   4860
gactaaaaaa cgaaggacaa tatgtagttt tcatatgcct ttacctttgc aatctccttt   4920
tttattgttt acccatactg gattaggttg gatttatcaa cacaaaatga gttggactat   4980
atcactacat tactgtggtc ctgtggatac atcaacaaaa aaaatgagtt ggaccatatc   5040
aatgtgttag cgtggattat gtacacattg gactggagtt gaagcaaata taatctgaaa   5100
agggcgatgg gttaggtcat gaggtattta gaataagact ttgatcaagc ccaaatccac   5160
ccgcaaagaa ttataccctt tattttcaag gcaccatcac tgcataaaat aatctgaaat   5220
gccacaaaag attaacgtcc aatatgctca cagccaaaaa tcaatccatt attgtttggt   5280
aagaaaaggt aataggctag atcaatttgc tgccaattgc caggcctgtg ggcctgtcac   5340
ctgtgggtaa tttaatatgn ctcaaatggg tcggcctgtt aagtacacca acatgaactt   5400
aaagctt                                                             5407
```

NEMATODE-RESISTANT GENE

BACKGROUND OF THE INVENTION

1. Field of the Invention

The present invention concerns a nucleic acid, which induces a resistance against sedentary nematodes in plants, preferably of the Solanaceae and/or Chenopodiaceae and/or the Brassicaceae families, especially preferably of the genus Beta and/or Brassica and/or Solanum.

The present invention additionally concerns the DNA sequence of a cDNA clone and a genomic clone of this nucleic acid. Further, the present invention concerns a vector, which can for example be a yeast artificial chromosome "YAC", which contains the nucleic acid for a resistance against sedentary nematodes in plants. Finally, the present invention concerns the use of the nucleic acid or of the vector for the induction of a resistance against sedentary nematodes in plants, and also a transgenic plant, which contains the nucleic acid or the vector.

Further, the invention concerns the protein encoded by the nucleic acid, a test kit containing the nucleic acid and/or the vector and a process for producing a transgenic plant and also a process for producing a nematode resistance in plants.

Finally, the invention concerns the promoter of the resistance gene.

2. Description of Related Art

It is well known that plants are attacked by various pathogens and types of parasite. It is also well known that crop plants are mostly more susceptible to parasitic attack than their wild relatives. Often encountered are plant parasites from the nematode family, with a fluid-filled pseudocyloma sheath surrounded by a musculocutaneous sac. Nematodes are important parasites, which in the harvests throughout the world cause losses of ca 150 million DM per year. Particularly damaging are nematodes of the genera Meloidogyne, Heterodera and Globodera, which establish themselves permanently in the roots of the affected plants, after they have induced certain feeding structures. The nematode *Heterodera schachtii* has a broad host spectrum, which includes many species of various plant families, e.g. the Chenopodiaceae and Brassicaceae.

The life cycle of nematodes is subdivided into four larval stages (J1–J4). The roots are infected by J2 juvenile stages, which migrate to the central cylinder, where they induce the development of syncytia. These extensive feeding structures result from a partial cell-wall degradation between the cells of the xylem parenchyma. The nematode ends its life-cycle to the adult stage after three periods. The female nematodes swell up and finally destroy the root cortex, while they are still feeding from the syncytia. The male stages no longer feed after the end of the third stage, and when they are adult they move towards the female stages, by which they are attracted by sex pheromones. The mature female stages are filled with eggs. After their death, they form a cyst, in which the infectious larvae (J2) can survive in the soil for up to 10 years.

It is presumed that nematode resistance genes trigger an incompatibility reaction between the host and the parasites, which has already been described at the cellular level. The roots of plants which carry this or these gene(s) are admittedly attacked by J2 juvenile stages, but most of the nematodes die in the late J2 stage because of degradation of the initiated syncytium. In rare cases, female stages can develop, however they display a transparent appearance and cease growing. As a result, the nematodes are not able to complete their life cycle.

Since for environmental political reasons the use of nematicides is only possible to a limited extent, it is particularly desirable also to implement this resistance gene in crop plants.

In particular, root crops of the genus Beta (e.g. sugar-beet, fodder roots, mangold, beetroot) are highly susceptible to the root cyst nematode *Heterodera schachtii.* Efforts have already long been made to create resistance against *Heterodera schachtii* and other phytopathogenic nematodes (e.g. Globodera) in plants, in particular crop plants, since resistance genes corresponding to these are lacking. The only sources of resistance are the wild species *Beta procumbens* and its close relatives *B. webbiana* and *B. natellaris.*

Genes for resistance against various nematode species are used in breeding in different useful plant species (e.g. potato, tomato, wheat, oil radish). A resistance gene from the wild species *Beta procumbens* has also been transferred into the sugar-beet by cross-breeding. From this, resistant sugar-beets could be selected; however, they had the disadvantage that they were characterised by inadequate quality and productivity properties. The resistant sugar-beet lines which derived from the cross-breeding with *Beta procumbens* have translocations of varying size from the wild beets of the Procumbentes section. Their low productivity and decreased quality are presumably due to the fact that as well as the resistance gene other productivity-decreasing genes from the wild species are present in these sugar-beet lines. Also, the transmission of the resistance property to subsequent generations is incomplete. These disadvantages cannot be eliminated purely by breeding methods, since breeding by crossing is unlikely to be able to select specific properties, without other, sometimes disadvantageous, properties also being transferred at the same time.

Further, many attempts have been made to induce artificial nematode resistance in plants by a combination of "suicide genes" with syncytia-specific promoters. So far, however, it has not been possible to breed any resistant plants from this.

Moreover, it has not previously been possible to identify a naturally resistant gene at the molecular level and to use it for the creation of a resistance in crop plants.

SUMMARY OF THE INVENTION

It is, therefore, one objective of the present invention to provide a nucleic acid which imparts a resistance against nematodes to plants. It is a further object of the present invention to provide the DNA sequence on which this gene is based.

Also, it is a further object according to the present invention to enable the use of such a gene for the induction of a resistance against sedentary nematodes.

Apart from this, it is an object according to the present invention to provide a transgenic plant which contains a nucleic acid imparting such resistance, and cells, seeds or plant parts which contain this nucleic acid.

Finally, it is an object of the present invention to provide vectors in which the gene for imparting resistance against nematodes can be effectively incorporated into plants and is contained therein.

It is a further object according to the present invention to provide the protein encoded by the nucleic acid and a test kit which contains the nucleic acid.

Finally, it is an object according to the present invention to provide a process for the production of a transgenic plant and a process for producing a resistance against nematodes.

It is also an object of the present invention to provide the promoter which controls the expression of the aforesaid resistance gene.

These and other objectives are achieved by the subject matter of the invention contained in the claims.

BRIEF DESCRIPTION OF THE DRAWINGS

FIGS. 2A and 2B show the nucleic acid sequence of SEQ ID NO:2.

DETAILED DESCRIPTION OF THE INVENTION

Figure 1:
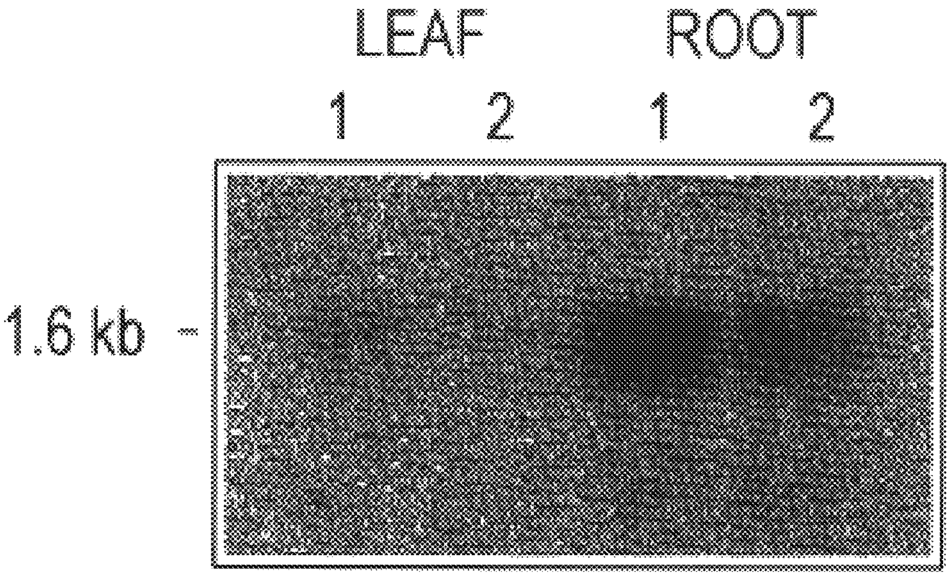
FIG. 1 shows a Northern analysis of total RNA from leaves and roots. The total RNA was isolated from leaves and roots of six-week old plants, which were either (1) infected or (2) not infected. The full-length cDNA 1832 was used as probe. 20 μg total RNA were separated in 1.3% agrose and transferred to nylon membranes. The filter was hybridised overnight at 60° C. with the radioactively labelled probe and then washed for 2×30 min at 60° C. in 0.2×SSC.

According to one embodiment of the present invention, a nucleic acid is provided which induces a resistance against sedentary nematodes in plants, preferably of the Solanaceae and/or Chenopodiaceae and/or Brassicaceae families, especially preferably of the genus Beta and/or Brassica and/or Solanum. The provision of such a gene makes it possible to breed crop plants which display a resistance against sedentary nematodes. Such resistant crop plants are of course far superior to their non-resistant relatives, since they cannot be attacked by nematodes and hence are less susceptible to disease. Through the provision of the nucleic acid which carries the resistance against sedentary nematodes in plants, it is further possible to obtain resistant plants which nonetheless display quality and productivity equal to that of other, non-resistant crop plants. This is attributable to the fact that a single nucleic acid, namely the nucleic acid for the resistance against sedentary nematodes, is transferred into the plants, whereas with conventional breeding procedures in addition to the desired genes other DNA sequences, which may code for undesired properties, are also transferred.

Especially preferably, the nucleic acid which induces the resistance against sedentary nematodes includes a translated region which is at least 60% homologous with the $Hs1^{pro-1}$ gene from *Beta procumbens*. Among these, inter alia, are the homologous genes from *Beta webbiana* and *Beta patellaris*. *The* $HS1^{pro-1}$ gene from *Beta procumbens* carries a resistance against sedentary nematodes in plants. A 60% homology with the DNA sequence cited above is already sufficient to induce the desired property of resistance against sedentary nematodes in a plant that carries this nucleic acid. Genes according to the invention are also obtainable by screening gene libraries with the sequence 1832, for which the hybridisation conditions can be chosen as follows:

Hybridisation temperature 50° C., preferably 60° C., and washing of the filters in 0.5×SSC, preferably in 0.2×SSC for 30 minutes for example.

Especially preferred is the nucleic acid which induces a resistance against sedentary nematodes in plants, which includes the following DNA sequence (SEQ ID NO: 2):

```
ATGAGAAGGT
GTGGGTATAG TTTGGGCCTT GGTGAGCCCA ATTTGGACGG AAAGCCCAAT
TTAGATTACG ACGCCGTTTG TCGTCCTTCT GAGCTTCACG CGCTTAAAAA
GGGCGCGTTG GATTATATTC AGAATTCGGA AAATCAGATA TTGTTTACAA
TTCATCATGA TTTTCGAGTC GTGGATTTTT TCCTCGAAAA ATTGTTGGAT
CGAATAAGTG AGAGGATCAG TAAAGAAGAG TTTACCAAAG CAGCAGATGA
TTGTTGGATA CTGGAGAAAA TATGGAAGTT ATTGGAGGAA ATCGAGAATT
TACATTTATT AATGGATCCT GACGATTTCC TGCATCTGAA GACGCAACTG
AGGATGAAAA CAGTGGCGGA TTCTGAAACT TTTTGTTTTC GATCAAAAGG
ACTGATCGAG GTAACAAAAT TAAGCAAGGA TCTACGGCAC AAGGTGCCGA
AGATCCTTGG TGTAGAGGTG GACCCTATGG GAGGACCGGT GATACAAGAG
TCGGCAATGG AGTTGTACCG AGAAAAAAGA AGATACGAGA AGATACATCT
GTTACAAGCG TTTCAAGGGG TGGAATCCGC TGTTAAAGGG TTTTTCTTTA
ATTATAAACA GTTGTTGGTG ATCATCATGG GTAGTTTGGA AGCGAAAGCG
AATTTTGCTC TGATTGGTGG TTCTACTGAG TCTTCGGATT TGTTGGCTCA
GTTGTTTTTA GAACCTACTT ATTATCCGAG TTTGGATGGT GCCAAGACTT
TTATTGGTGA TTGTTGGGAG CATGATCAGG CTGTTGGTAG CGGCCTCGAT
TGTCGTCATC ATCGGAAGAA TCGGACTGCG AAACAATGA
```

This sequence will be referred to below as No. 1832.

Also covered by the present invention are nucleic acids which encode a protein which imparts the same nematode resistance as the gene product encoded by the above nucleic acid No. 1832, where preferably all these gene products include the same amino acid sequence.

Preferably, the nucleic acid is a cDNA.

In a further embodiment, the nucleic acid which induces the resistance against sedentary nematodes in plants is a genomic DNA, which includes the following DNA sequence (SEQ ID NO: 1):

```
TCTAGAGCTG TCGACGCGGC CGCGGAATTA ACCCTCACTA AAGGGAACGA
ATTCGGATCT TCTTTCTTGG TGCTTAATTT TTTGACACTA ATCCGATTCT
TAGCATTAAG TTGAAGCACA CTCTTGATAA ACTATGTTAC TATGTATCAT
TGTCAATATG CTAAGAATTT GTCTTGACCT CATCGCTATG TATAAGCATC
TAATACTTTC CTAAACTAGT AAAAACAAAT ATTCCATCCG TCCCATAATA
TGACTCCCCT TTCTATTTTA GGAGTCAAAA TTTTAAAATT TTTGACCAAA
TATTCTTATT ACTATATATA AAAACATATT CATGTGGGAT CTTGTTAGAT
TCGTCTTAAT ATGTATTTTC ATAATATCAA CTTTTTATAT TTTTTTACTA
ATACGAAATT GAAGATATAC AATGTCTTAA AGACTATGCA AAACTAAGCA
GAACCTATAT TTTGGGACGG AGGGAGTAAT AAGTAATATT GATTGACGCA
TAATTTGTAT ATAAATATTT CAAATTGATA CTACTTTAAA TAATATAGTT
AATGCTTATA AATAAGCCTA AAGACTGTGA ATAGCAAGAT CGTTAAAAAT
AAAATTTGAA AATATTTGAT ATGGATAATG AAATTGGAAA TGGCATGCTT
AGCTTCTCGG GAATCTTATA CCGCTACATC TATAATAAAA ATTCCTCATA
AAATTTTGAA CATTTTAACA CACGAAATTC GTCCTTTTAC GCGAGCCCTT
TCCACACGTA TTTAAAATTT AAAAACCTCG TCTTTACTCT CCCCACCTAT
ATATATACAC GTCCCCCCTT CTCTACTTCC CATCTCACAT ACACATACCC
AATCCACAAA CTTCCATCTT ATCCAACTTT CTCTCACCTA TCTCCTTCTT
CAATTTTCAA AACTCAAAAG AAAATGGTAG ATTTCGATTG CAAAACAAAA
ATGGTACAAT CAACACCAAA CCTCACAAAA AAATCTCCAA AAATCACAAC
CAAACGCACA ATATCAACAC CATTAATTTC ACCAGTACCA GTAATTTCCG
GCGAATTATC TCCGGCGTCG GAATCATCCT GTTCAGCTTA CGAATCGTAT
CTCAAATTCA CGGAGCTCCG TCAACTATGG AGTTCAAAAG AATTCCCCGG
TTGGGATAAC GAACCGATAA TCAAACCGGC TTTGCAAGCA TTAGAGATAA
CATTCCGGTT CATCTCACTC GTTTTATCCG ACGCTAGACC GTACATAAAC
CGGCGAGAAT GGAACCGGAA ATTAGAGTCG TTAGCGAGAG ATCAAGTCCG
AAACTCATCT CAGTTCTCTG CGGAAGACGA TGAGACACGT GGATCAGCTC
CGAATCGTTG ATCTGACGTC ATCGTATGGT GAGGTGATGT CACAAACAGA
AGTTCAGCGG AGGTATGGAA GCTTGCGAAT GGAGAAGATG ATACTACCGT
GGTCTGTCGT AGTAGCGAAT TTAGTCTCCT TCCGAGGTTA GCCACGTGGC
AGAAGTCGGA GGAGATTGCT TCTAGAATCT TCTACGCGGT TGAATCTGCT
ATGAGAAGGT GTGGGTATAG TTTGGGCCTT GGTGAGCCCA ATTTGGACGG
AAAGCCCAAT TTAGATTACG ACGCCGTTTG TCGTCCTTCT GAGCTTCACG
CGCTTAAAAA GGGCGCGTTG GATTATATTC AGAATTCGGA AAATCAGATA
TTGTTTACAA TTCATCAGAT TTTCGAGTCG TGGATTTTTT CCTCGAAAAA
ATTGTTGGAT CGAATAAGTG AGAGGATCAG TAAAGAAGAG TTTACCAAAG
```

-continued

CAGCAGATGA TTGTTGGATA CTGGCGAAAA TATGGAAGTT ATTGGAGGAA
ATCGAGAATT TACATTTATT AATGGATCCT GACGATTTCC TGCATCTGAA
GACGCAACTG AGGATGAAAA CAGTGGCGGA TTCTGAAACT TTTTGTTTTC
GATCAAAAGG ACTGATCGAG GTAACAAAAT TAAGCAAGGA TCTACGGCAC
AAGGTGCCGA AGATCCTTGG TGTAGAGGTG GACCCTATGG GAGGACCGGT
GATACAAGAG ATGGCAATGG AGTTGTACCG AGAAAAAAGA AGATACGAGA
AGATACATCT GTTACAAGCG TTTCAAGGGG TGGAATCCGC TGTTAAAGGG
TTTTTCTTTA ATTATAAACA GTTGTTGGTG ATCATGATGG GTAGTTTGGA
AGCGAAAGCG AATTTTGCTG TGATTGGTGG TTCTACTGAG TCTTCGGCTT
TGTTGGCTCA GTTGTTTTTA GAACCTACTT ATTATCCGAG TTTGGATGGT
GCCAAGACTT TTATTGGTGA TTGTTGGGAG CATGATCAGG CTGTTGGTAG
CGGCCTCGAT TGTCGTCATC ATCGGAAGAA TCGGACTGCG AAACAATGAT
GGTTTCGAAG TTAGTTTTGG ATTGAGTTTG GTTTGATCTG ACTCGGCTGA
GTAATGGGCG GCGATAGGGA GGTTATGGAG AACGTGGGGC GGAAAGTGGG
TGGCCTTGTT AGTGAGACGT GCAAACTTTG GTTACTATTA CATGTGATAT
ACTTATATTT AGTGGGAATA TTGCTTTGGT GTATATAGAT AAATTTTTGA
ATTAATTGTT ACACTTGTAT TAGTAAATTC TGTATCATGA TGATTATAAC
ATGAATTTTT TGTTGTGACT TTAAATGAGA TTTATGCTCC TTAATCCTTA
TTTCACTGAT ATTATTTTTT TGTAGTCTGA GTATAAGTGC GGAGTTTAAT
CAAGCAAGAG AAAATAATAG AAGGTGATTG CATACTTGGA TTGGAGATCA
ATATCTAAAA GATGGTTATG AAACTATTGT GAATAACGGA GTACATGTCC
AACACCACAC ACGTATGACT GTGTACCTCT AATTTACAAA GAGATTTACA
AAATCTAGAT GAGTTTTGAT ATGATCGACA TTGTCTCTAA ATGGGAGATA
AGAATTAAAT CGTCAGGCTC TTTGCGGCTA G?TCTTCCGA ATAAAATAAG
AAACAATGGT TTACTCTAAT TCA?TTTTCC AATTGGCAAA GTGGCACAAG
CTTCAATAA? T?GGCTCTTC ACAATTGAGT ATAAAAGAAT GGGTTAATTA
C?CCGG?CTT TGAATAAAAT TAATCCTATT TAATTGTTTT TGAAATATTC
TTAAAAATA? CGTTGTCTAA TACTTTCTTT AGTTGGGACC CGGTTCTGAA
CC?ACTTAAA TTAATGGGCT CAATGGCCGC CTAATTTCCT CTTGTTATTT
TTAGCCTTTT TTTTCCTTTT TTTCCCTTTA AAATAACTAT TTGTTCTCTT
GAATATCTTA AAATACGTGT GTATC??CTT TAGTTGGACC GTCTGAACTA
TTATTATGCT ATGCACTATT CCTTTGTATT TACCTTTTTC TTTTTCCTTT
AAATACTATT GTTCTCATTT CAATTATATT CTATTTTTGT TAAAAAACGG
TCTTAATTTT TACAACAGTA AAATTATTGA TTTTCCTTCT ATATTAAAAT
TTGAAAGTGA ATGTATTTCG AAATTTAGGT ATATGAATAT TTATATTGTT
CGATTAATGA TGATAAAAGG ATTTTACTCA TTAACCTAAA CCATTTCTAG
ATAAGATAAG AGGAACTTCC ACCTAGTTAA CATGTCTCAC TTTCCTAGTA
GACGAATCTC AATTGCGTTG CTGGATTTAG AACTTTGGTC AAGATAATGG
CAAAACTTTC AAGCACCCGT AGATGCATTT TCC?CGACAT TTCTCATACA
GCACTAAACG TTTCAACTTC CTCTTTTATT TTCTTGAAAT TTTTTGTGGC

-continued

```
AATGAGAAAC GTTCGAAGTT GATCTTTGCG TTTCGACGAT TTGAAATAAG
AAAATGCGTA TTGTCGGCAA CTGATTGTAG TAGTTGA?GT TATTATAATG
ATAGTCTTTT ATATAGAATT CATTTAATTC TAATTCATTT GAATCCAGTT
AAGTTGAGTT TAGTTTAGTC AGCCTAAAAG AACAAAGTAA GTCATGGAAT
GGAATGAAGA TGTAATCAAA TAGAGGAGGG GCTGATAACA ATAATTATTA
CTTATGTTGC GTGTTCAATT CAGTAATGAA AAAAATAAGG TTGAATTAGG
AGGGTAATAC AATTATTACC GGTGATGTGA TAAAACTAAT GTTTAAGGGT
TTAAGTTACT CTAAACCCTC AATTAAACAT AGTCTAACAA AAAATTCTCA
TAATCTAAAT CAAACACGTA CTTATACAAT CCTCTACATG AATCCGTTTC
TAACTCTAAA GGAAGATCGA TACTTATTAG AATCCGTTTC CAACCCTAAA
AATGACTGAT CAAAGGTTCA TGGATTTTGG AAGGGAAAGA CGAATGCGAG
GGCAGTGTAC AGGATAATGT GCATGAGATC GCAAGGGTCA TGCTAGTTAG
AGCAAAATAT A?ATGACTTA ATTCAAAAAC TACCTACTAT TTCAAATTAA
TAGACTTTAT TGGAGTCATG AAGTGTACTG TTTGGTACAC CCCACATTAC
TCATGCACTA CACCTAATTT GTCACAGCAT TCAGCTGCCC TTGTTTTGCA
GTCTTTGGAG CTGGCGTGCC TGTTGTTGCT GGTTAGTCGG CGCTTGGTCT
GTTGTG??GT GACCCTCTGT TTTTTTTTTT TTTTAAAATG GTCGCTGATT
ACTAT?CTGT GTATT?CATT TTGTACTCCC TCGTATCCAA TTATATGCTA
CACTTTTTTT GCGGACTCCA AAACGTTTTT TTTTT?TGTC CGAGAGATAG
AGAGGAAAAG CCCATGTTGT TAGGAGAGAG ?TCGGGAGAA GGAAAAGCCA
AATAAAGAAG TAATAACATC TAAATAAGAA AATTCCTTTG ATGGAAAGTG
TAGCGACTAA AAAACGAAGG ACAATATGTA GTTTTCATAT GCCTTTACCT
TTGCAATCTC CTTTTTTATT GTTTACCCAT ACTGGATTAG GTTGGATTTA
TCAACACAAA ATGAGTTGGA CTATATCACT ACATTACTGT GGTCCTGTGG
ATACATCAAC AAAAAAAATG AGTTGGACCA TATCAATGTG TTCGCGTGGA
TTATGTACAC ATTGGACTGG AGTTGAAGCA AATATAATCT GAAAAGGGCG
ATGGGTTAGG TCATGAGGTA TTTAGAATAA GACTTTGATC AAGCCCAAAT
CCACCCGCAA AGAATTATAC CCTTTATTTT CAAGGCACCA TGACTGCATA
AAATAATCTG AAATGCCACA AAAGATTAAC GTCCAATATG CTCACAGCCA
AAAATCAATC CATTATTGTT TGGTAAGAAA AGGTAATAGG CTAGATCAAT
TTGCTGCCAA TTGCCAGGCC TGTGGGCCTG TCACCTGTGG GTAATTTAAT
ATG?CTCAAA TGGGTCGGCC TGTTAAGTAC ACCAAGATGA ACTTAAAGCT T
```

At positions marked by (?), A, G, C or T may be present, or the nucleotide is not present. The translation origin is underlined. The bold-printed letters represent the cDNA fraction. In the attached sequence protocol, (?) corresponds to the letter N.

This sequence will be referred to below as No. 1832.1. The original sequence of 5407 nucleotides, as stated in FIG. 2 (SEQ ID NO: 7), contained sequencing errors, which do not however affect the protein-coding region.

Finally, the present invention includes the sequence according to the Seq.Id.No.3 (also referred to as 18832A1).

Also included is a nucleic acid which is obtainable by screening a DNA library with a DNA sequence such as described above and which codes for a nematode resistance, as demonstrated for clone 1832.

Preferably the nucleic acid derives from a wild species of the section Procumbentes of the genus Beta.

Especially preferably, the nucleic acid, as described above, induces resistance against sedentary nematodes of the genera Meloidogyne, Heterodera and/or Globodera. In particular, the induction of resistance against *Heterodera schachtii* in plants is preferred. Especially preferably, the resistance is induced against sedentary nematodes in plants of the species *Beta vulgaris.*

On the incorporation of such a gene into the plants to be modified, as a rule only the property nematode resistance is influenced. No pleiotropic gene effects are to be expected. Thus the productivity of the breeding stock remains unaffected. The transgenic plants that express the aforesaid gene display an incompatibility reaction towards cyst nematodes. As a result they can be used for the breeding of resistant varieties. As this is a natural resistance nucleic acid from wild species of the section Procumbentes of the genus Beta, no acceptance problems as regards genetically modified plants are expected. Nematode-resistant varieties which have the aforesaid gene can lead to an increase in the proportion of host crops in the rotation of crops. In the case of the sugar-beet, this theoretically means that a crop with a high rate of return can be cultivated to an increased extent. Further, the $HS1^{pro-1}$ sequence is active not only in plants of the genus Beta, but is also capable of producing a nematode resistance in plants of other genera, for example in *Arabidopsis thaliana.*

Whether a located sequence has the potential to impart nematode resistance to a plant can be checked by normal tests, such as are for example explained in still more detail below.

According to a further preferred embodiment of the present invention, a vector, especially preferably a yeast artificial chromosome (YAC), which imparts a resistance against sedentary nematodes to plants and contains the nucleic acid as described above, is provided.

The YAC can for example contain the following DNA sequence:

1. (No.1832)
2. (No.1832.1).

A 60% homology with the nucleic acids contained in the YACs suffices for the induction of a resistance in the plants.

Preferred YACs are as follows:

TABLE 1

| YAC | Size in kBp | Specificity | Cloned sequences of the YAC ends: left | right |
|---|---|---|---|---|
| YAC42D12 | 50 | 643 | − | + |
| YAC112G9 | 60 | 643 | + | + |
| YAC120E7 | 150 | 643 | + | + |
| YAC31G11 | 70 | D13 | + | + |
| YAC80G3 | 200 | YAC31L | − | + |
| YAC116C5 | 50 | YAC31R | − | − |
| YAC114H8 | 120 | YAC104L | − | − |

In a preferred embodiment, a resistance against nematodes of the genera Meloidogyne, Heterodera and/or Globodera is induced in plants. Especially preferably, the resistance is targeted against *Heterodera schachtii.*

Preferably the resistance is induced against sedentary nematodes in plants of the species *Beta vulgaris.*

Further, the invention is directed to the use of the nucleic acid or the vector, as described above, for the induction of resistance against sedentary nematodes in plants.

Apart from this, the invention is directed to transgenic plants which contain the nucleic acid or the vector as described above.

The gene can be expressed in plants by transformation by standard methods either under the control of a constitutive promoter or under the control of the internal promoter which ties upstream of the translated sequence. As a result of this, an incompatibility reaction with the sedentary nematodes, in particular the cyst nematode *Heterodera schachtii* is caused.

The upstream-located promoter region of the gene, including ca. 1500 nucleotides, can be used for the root-specific expression of any gene in any plants. Included are promoters which derive from the 5' non-translated region of the $HS1^{pro-1}$ gene and show the same promoter activity as the $HS1^{pro-1}$ gene promoter.

A preferred promoter is situated within the XbaI fragment between nucleotide positions 1 and 1521 in the sequence 1832.1. Further preferred are promoters which are derived from the said promoter by for example insertions, deletions, substitutions and/or inversions and have the same promoter activity or even show stronger promoter activity. The presence of promoter activity can be identified by the usual procedures, as for example described below by means of the examples.

Derivatives of the aforesaid 1832-promoter that display at least 10% of its promoter strength are regarded as being according to the invention.

Thus for example the 1832 promoter is activated in *Arabidopsis thaliana* with the result that the sequence 1832 under the control of the said promoter causes resistance against *Heterodera schachtii* in this host.

In a preferred embodiment, the transgenic plant belongs to the genus Beta or to the genus Brassica. Especially preferably, the transgenic plant belongs to the species *Beta vulgarism.*

The invention is also directed to cells, seeds or plant parts which contain the nucleic acid or the vector as described above.

Further, the invention is targeted on the protein encoded by the nucleic acid, and also on derivatives thereof with the same resistance-imparting properties.

The proteins according to the invention are obtainable by expression of the nucleic acid according to the invention in a suitable host such as bacteria, yeasts, mammalian and plant cells.

Apart from this, the invention concerns a test kit, which contains a nucleic acid or a vector, as described above, or a protein, as described above. Further, the invention concerns a process for the production of a plant, characterised in that a nucleic acid, as described above, is introduced into a plant cell and a plant is regenerated from the plant cell.

Further, the present invention concerns a process for producing a nematode resistance in plants, which is characterised in that a nucleic acid, as described above, is introduced into a nematode-sensitive plant.

Apart from this, the invention concerns a promoter which also controls the expression of the nucleic acid described above and that is characterised in that it is active root-specifically.

The 5'-flanking region of the gene, a ca. 1.5 kb XbaI fragment, contains typical elements of eukaryotic promoters, such as for example the TATA box. The promoter is apparently root-specific, since after Northern analysis with leaf- and root-RNA, a signal was only found with root-RNA. This is also confirmed by experiments with transgenic potatoes, which had been transformed with a fusion product from the 1832 promoter and the GUS gene. There the roots showed a clear colour reaction, which indicated activity of the 1832 promoter.

Hence the 1521 nucleotide-containing 5' region of the 1832 gene and derivatives thereof with similar promoter activity can be used for the expression of any genes, especially in root tissues, of different plants. Suitable derivatives are those which display at least 10% of the promoter activity of the 1832.1 sequence. Examples of applications are the expression of genes for resistance against nematodes and also resistance against other root-borne pests, and expression of genes which are involved in sucrose translocation and generally of genes which are involved in sucrose or inulin storage. Derivatives of the promoter according to the invention are sequences which are derived from the promoter of the 1832 gene for example by deletions, insertions, base exchanges, etc., where the promoter properties of the 1832 gene promoter are retained.

Finally, the invention concerns a primer for the PCR, obtainable from the sequence No.1832.1.

Below, the invention is described in detail on the basis of examples, but these examples are not intended to limit the scope of the invention.

EXAMPLE 1

Cloning, of the $HS1^{pro1}$ Gene

For the cloning of the $HS1^{pro1}$ gene, closely interlinked markers were identified. A *B. pro-cumbens*-specific satellite (pRK643) was cloned from one of the fragment-addition lines. A Southern analysis showed that all tested resistant lines carried this satellite, which indicated that it is distributed in the region of the genome of the wild species *B. procumbens* in which the gene is located. This marker was found helpful in the identification of the translocation line with the smallest segment of the wild beet among a large number of chromosomal mutants. This line was selected for the positional cloning of the gene. The marker pRK643 cosegregated perfectly with the resistance in a segregating F2 population of 241 individuals. Using this satellite marker as probe, 3 clones which included the $HS1^{pro-1}$ gene region were extracted from a YAC library of the line A906001.

EXAMPLE 2

Identification of the Transcribed Sequences of the YACs

In order to identify the transcribed sequences of the YACs, a cDNA library from the roots of A906001 plants infected with nematodes was created and screened with the three YACs, which leads to the isolation of three cDNA clones, namely numbers 1832, 1845 and 1859. The clone 1845 showed a cross-hybridisation with sugar-beet DNA, while the clone 1859 gave multiple band patterns with the DNA of both susceptible and also resistant beets. The further work was concentrated on the cDNA 1832, since:

1. This cDNA yielded a single-copy signal with DNA of the resistant lines, while no signal was visible with DNA from the susceptible sugar-beet, which allows the assumption that this gene is not present in cultivated root tubers. All monosomal addition lines which carried the $HS1^{pro-1}$ gene yielded a signal with this probe.
2. It showed complete cosegregation with the resistance property in the segregating F2 populations.
3. A ca. 1.6 kb transcript was only present in roots of resistant plants, as was shown by Northern analysis. A markedly stronger hybridisation signal compared to non-infected roots was found with RNA from roots which were infected with *Heterodera schachtii.*
4. The sequence analysis of the aforesaid polypeptide showed motifs which are typical for resistance gene products cloned recently.

Taking these results together, the clone 1832 represented a wild-beet specific gene, which is only expressed in roots and is stimulated after nematode infection.

EXAMPLE 3

Genetic Complementation Analysis

Hairy root cultures were obtained by induction with *Agrobacterium rhizogenes* and used for the genetic complementation analysis. The hairy root cultures from the sugar-beet were found to be a suitable substrate for root pathogens. The compatibility reaction of the susceptible and also the incompatibility reaction of the resistant roots to cyst nematodes is maintained in hairy root cultures of the sugar-beet. A susceptible sugar-beet line (No.93161p) was transformed with the 1450 base-pair (bp) cDNA 1832 using an *A. rhizogenes*-mediated gene transfer. The genetic engineering modification of the transformands was confirmed by GUS assay and DNA blot analysis. After inoculation with J2 juveniles, six mutually independently transformed roots were found, which expressed the 1832 gene and showed the same incompatibility reaction as the resistant line A906001, while nematodes regularly developed on the susceptible controls and on the hairy roots which did not contain the gene. Susceptibility could be restored after transformation of a resistant root culture with an antisense construct of the cDNA 1832.

These experimental data confirm that the resistance in hairy roots from the line 93161p depends on the expression of the 1832 gene. The isolated gene is designated $HS1^{pro-1}$ gene since it transfers the nematode resistance to the susceptible sugar-beet line in such a way that it completely matches the resistance in the line A906001.

EXAMPLE 4

Sequencing of the cDNA

The sequencing of the whole cDNA and of the corresponding genomic clone showed an open reading frame of 846 bp with no introns, which encoded an aforesaid gene product of 282 amino acids, which agrees with the data obtained from the RNA blot.

EXAMPLE 5

Structural Analysis of the Amino Acid Sequence

The amino acid sequence of the aforesaid polypeptide can be subdivided into four different subdomains. A putative signal peptide (domain A) can be defined at the N-terminus, which presumably has the task of leading the protein to the cytoplasm membrane. A leucine-rich region (domain C), which is arranged in imperfect, leucine-rich, repeating units, can clearly be discerned at the N-terminus of the $HS1^{pro-1}$ polypeptide. The repeating leucine-rich units (LRR) are part of the protein—protein interaction and were found in previously cloned resistance genes from plants, e.g. the RPS2 gene from *A. thaliana.* Their function varies from mutational recognition sites in receptor-like molecules which are located extracellularly, to catalytic domains of enzymes which are active in the cytoplasm. Similarly to other LRRs that have been identified in plant resistance genes, the LRRs of the $HS1^{pro-1}$ polypeptide are less conserved than the consensus sequence of the LRR consensus superfamily. The LRRs of the $HS1^{pro-1}$ polypeptide are characterised by a 20 aa consensus motif (SEQ ID NO: 6) (xLxxaxxaxLxxLxxaxxxL; L=leucine or isoleucine, a=aliphatic or aromatic aa, x=any aa). The leucine and aliphatic residues at the positions 2, 5 and 16 are located in the same positions as in the consensus of the LRR superfamily. The highly conserved asparagine at position C is replaced by a leucine/isoleucine. This asparagine is also lacking in the consensus LRR of the RPS2 polypeptide. The hydrophobic domain of 17 aa in the $HS1^{pro-1}$ gene (domain F) indicates a transmembrane segment. The C-terminal domain contains aa with positively charged residues and a putative N-glycosylation site.

The elicitor-receptor model of the plant-pathogen interaction suggests that the products of the resistance gene act as specific receptors for pathogenic triggers in accordance with the gene-for-gene hypothesis. The sequence analysis of $HS1^{pro-1}$ suggests that it is involved in a gene-for-gene resistance as part of a cascade of defence reactions. The aforesaid polypeptide consists of imperfect LRRs, which are located at the N-terminus with an additional signal peptide, a putative transmembrane-extending domain and a positively charged C-terminus, and thus fits into the second group of plant resistance genes.

Similar protein structures between $HS1^{pro-1}$ and the resistance gene Cf-9 from the tomato could be predicted, although no significant sequence homology was established. As the possible mode of the resistance reaction, the extra-cytoplasmic LRRs may act as receptor-recognising putative triggers. It is known that nematodes produce secretions which can interact with membrane-bound plant receptors. The positively charged C-terminus possibly interacts with the cytoplasmic components for the signal transfer. Alternatively, as a protein which is located in the cytoplasm, it may act as a receptor for triggers that have been injected into the cell via the nematode's oral barb.

Through the cloning of the first plant gene which is involved in nematode resistance, it should be more possible to understand the process of host-specific defence against nematodes. In addition, the isolation of the $HS1^{pro-1}$ gene offers the possibility of transferring a resistance to host species of agricultural importance, in which no allelic form of the gene is present.

EXAMPLE 6

Identification and Characterisation of the $HS1^{pro-1}$ Promoter

A ca. 1.5 kb XbaI fragment, which corresponds to the 5'-flanking region of the gene and the sequence with the number 1832.1, was isolated from a lambda-DASHII library using a PCR fragment from the 5'-region of the $HS1^{pro-1}$ gene. The isolated promoter sequence contains the typical elements of eukaryotic promoters, such as the TATA box with the sequence TACATAAA in position 23 before the transcriptional start site or the 5'-end of the cDNA.

The identified promoter is root-specific, since in Northern blots a signal with the probe from the 5' region of the 1832 gene is only found in root tissue.

Moreover, constructs containing the promoter according to the invention and a GUS reporter gene show a colour reaction exclusively in the roots of transformed potatoes or tobacco.

Furthermore, the promoter is inducible by nematodes. This is shown by a comparison of the transcriptional activity of sugar-beet roots infected with H. schachtii and non-infected ones. From this, it can be concluded that the promoter according to the invention binds to transcription factors which derive from nematodes or which are formed as a result of the infection.

The said experiments demonstrate the root-specificity of the $HS1^{pro-1}$ promoter.

EXAMPLE 7

Expression of the Sequence 1832 in Arabidopsis

The cDNA 1832 was fused with the GUS intron gene (Vancanneyt et al. (1990) MGG, p.245) and placed under the control of the 35S promoter. Using the vector pAM194 (described below), the construct was introduced into *Arabidopsis thaliana* by standard procedures by means of *Agrobacterium tumefaciens.* After three generations of selfing, lines were obtained which display complete resistance against *Heterodera schachtii,* i.e. no cysts or developed females whatever were observed. The resistance test was performed in a Petri dish with infectious larvae. The GUS activity was also determined.

EXAMPLE 8

Tissue-Specific Regulation of the 1832 Promoter

For the studies, the XbaI restriction fragment (XbaI-sites at positions 1 and 1521 of the 1832.1 sequence) was fused with the GUS intron gene and introduced into the roots of sugar-beets and potatoes by means of the vector pBIN19 and *Agrobacterium tumefaciens/Agrobacterium rhizogenes* cotransformation. In the sugar-beet, it was observed that in a "hairy root culture" the GUS activity was only detectable in the syncytium. In non-infected roots or in regions in which no nematodes were present, a corresponding GUS activity was not discernible. This shows that the promoter used has a "pathogen-responsive" element or elements, which is or are activated more strongly after nematode attack. Thus, the 1832 promoter enables the tissue-specific expression of any gene in host plants, such as for example the sugar-beet.

EXAMPLE 9

Expression of cDNA 1832 in Brassica

Rape cotyledons were transformed with a construct containing the sequence 1832, as described above in example 7. The cotyledons were cultured on MS nutrient medium, the selection on MS nutrient medium being performed by addition of carbenicillin. Examination of the transformands showed positive results both in the GUS test and also in the PCR analysis.

EXAMPLE 10

Identification of a Variant of Clone 1832.1, Referred to Below as 1832A1

Figure 3:
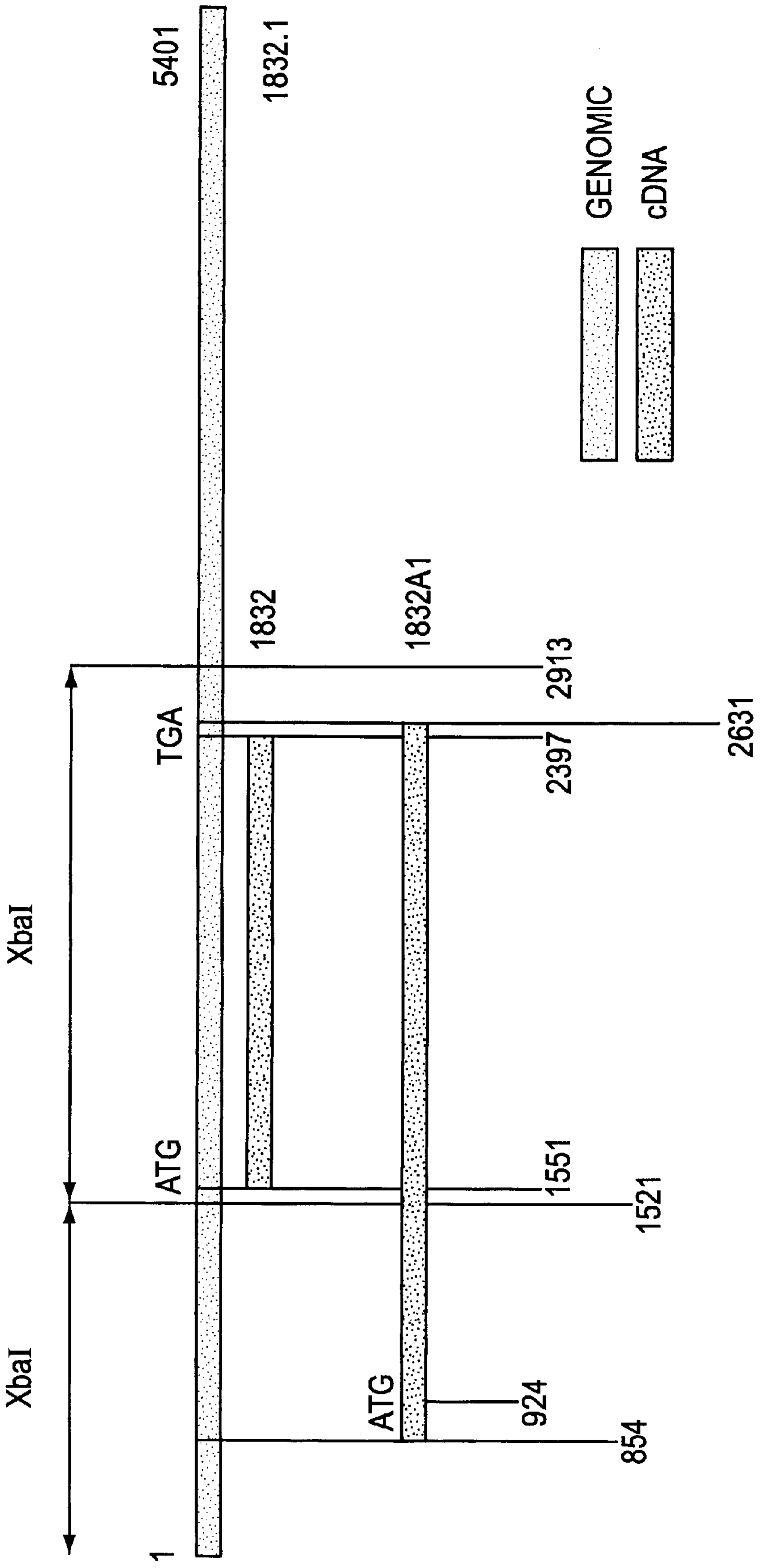
FIG. 3 shows schematically the encoding capacities of clones 1832.1, 1832 and 1832A1.

A variant of clone 1832 was identified, which includes an open reading frame, in which the start codon corresponds to the ATG at position 924 in the 1832.1 sequence. The stop codon corresponds to position 2397 in sequence 1832.1. The variant 1832A1 contains further slight differences compared to the sequence 1832. 1, as can be seen from the sequence comparison. Remarkably, after expression in host cells, all the sequences, i.e. 1832.1, 1832 and 1832A1, lead to resistance to nematode attack. Without being attached to one theory, it can be assumed from this that the shorter of the sequences, namely 1832, encodes all elements which impart to the encoded protein the ability to induce resistance against nematodes. FIG. 3 shows schematically the encoding capacity of the 3 clones 1832.1, 1832 and 1832A1 relative to one another. The section 1832 is common to all the clones.

EXAMPLE 11

Preparation of the Expression Vector pAM194

The binary vector prepared, pAM194, combines the properties of a cloning vector and a plant transformation vector (Ti-plasmid). Its suitability as a transformation vector was tested together with *Agrobacterium tumefaciens* and also in combination with *Agrobacterium rhizogenes* for cotransformation experiments. The vector is a derivative of PBI121 (Jefferson et al. 1987) (Clontech Laboratories); the backbone for pBI121 is provided by pBIN19 (Bevan et al. 1984).

Figure 4:
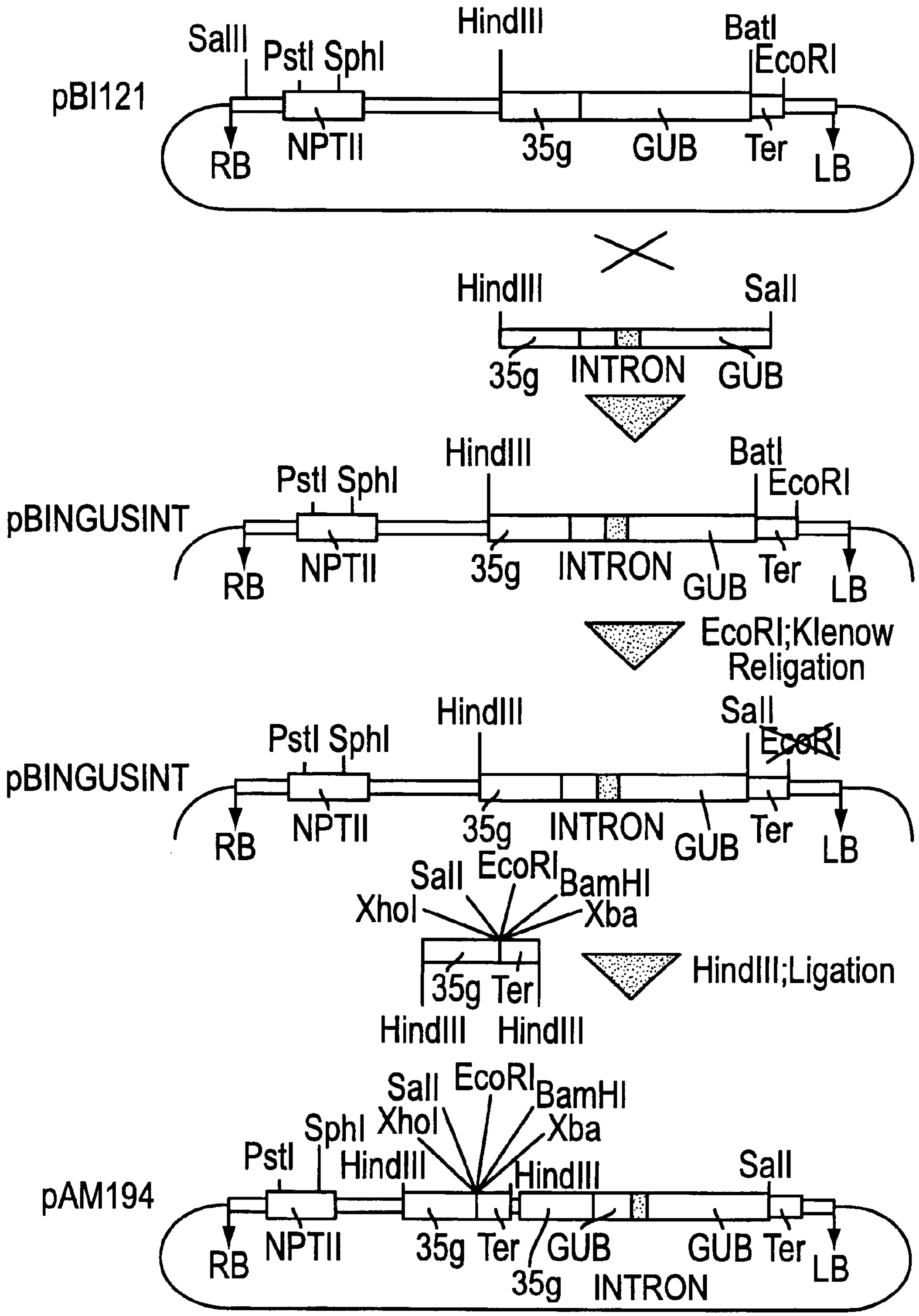
FIG. 4 shows the elements contained in pAM194
Figure 5A:
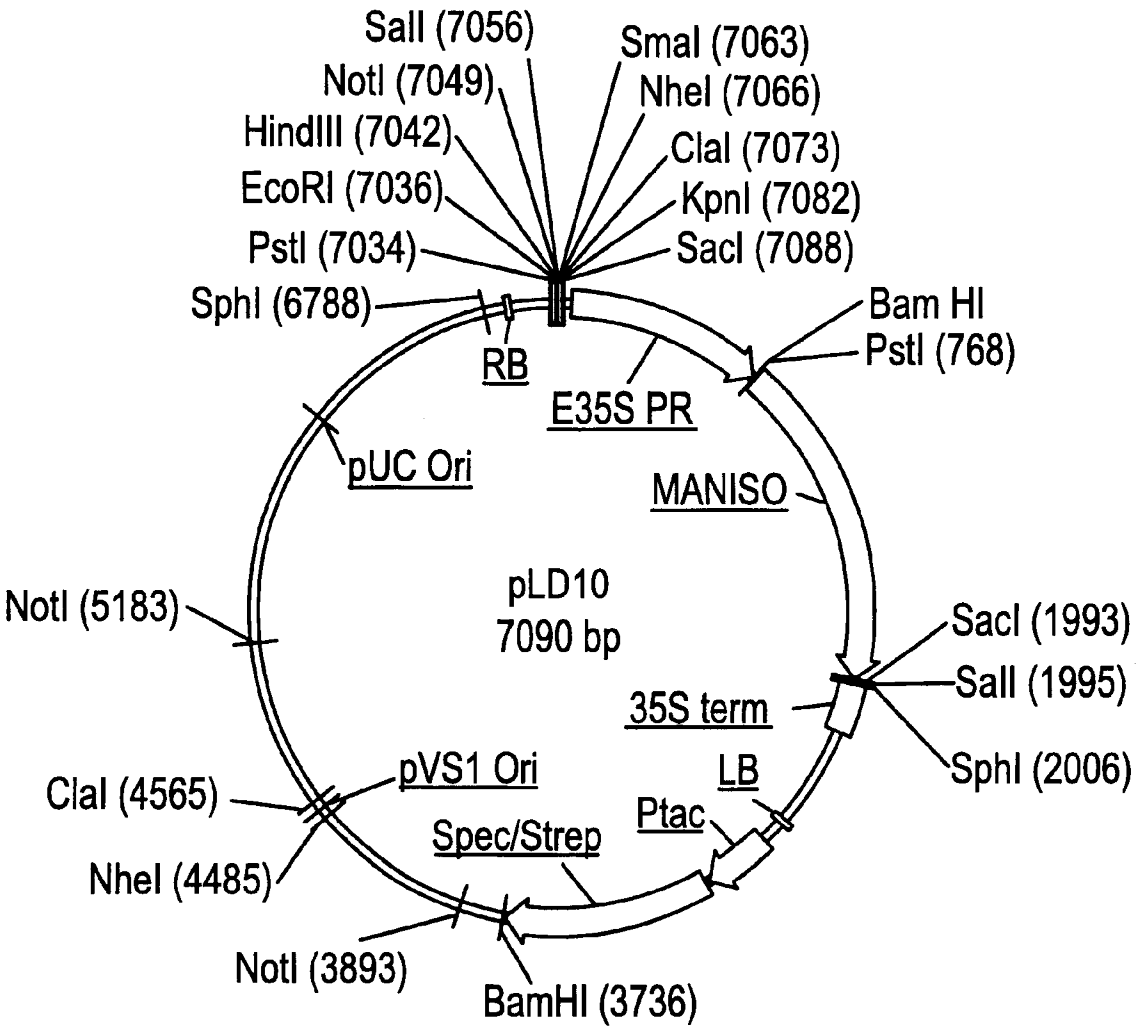
FIGS. 5*a–d* show the restriction site map of constructs pLD10, pPS48, LD10/1832-13, and pPS48/BamHI-15, respectively.
Figure 5B:
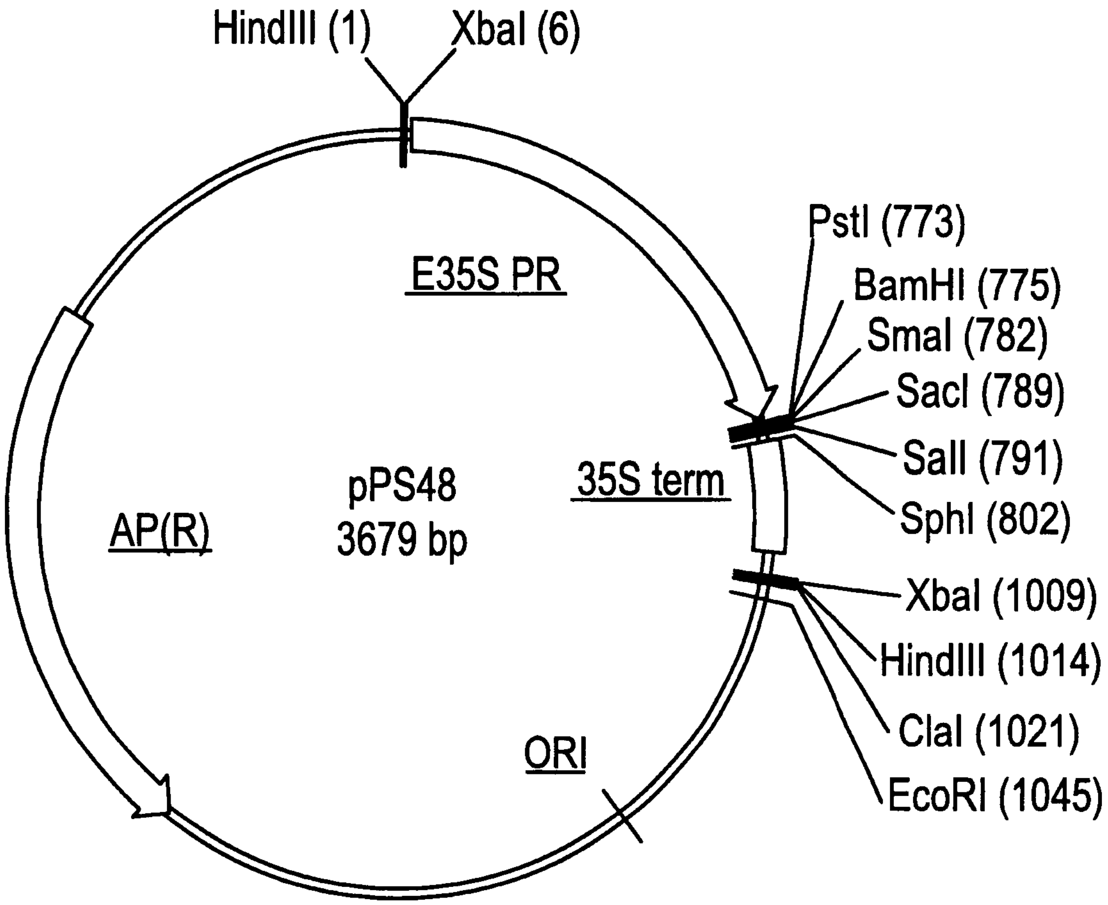
Figure 5C:
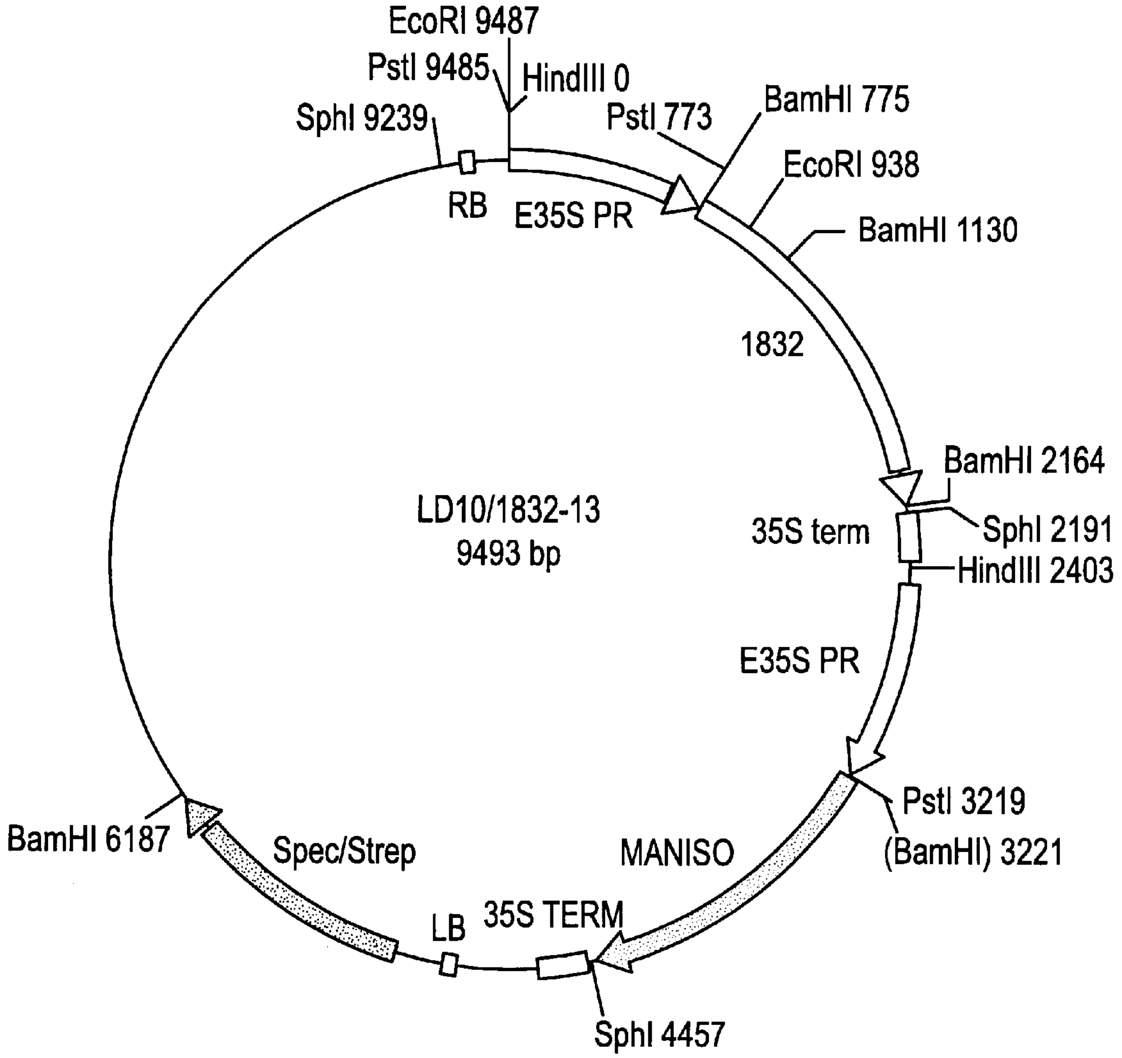
Figure 5D:
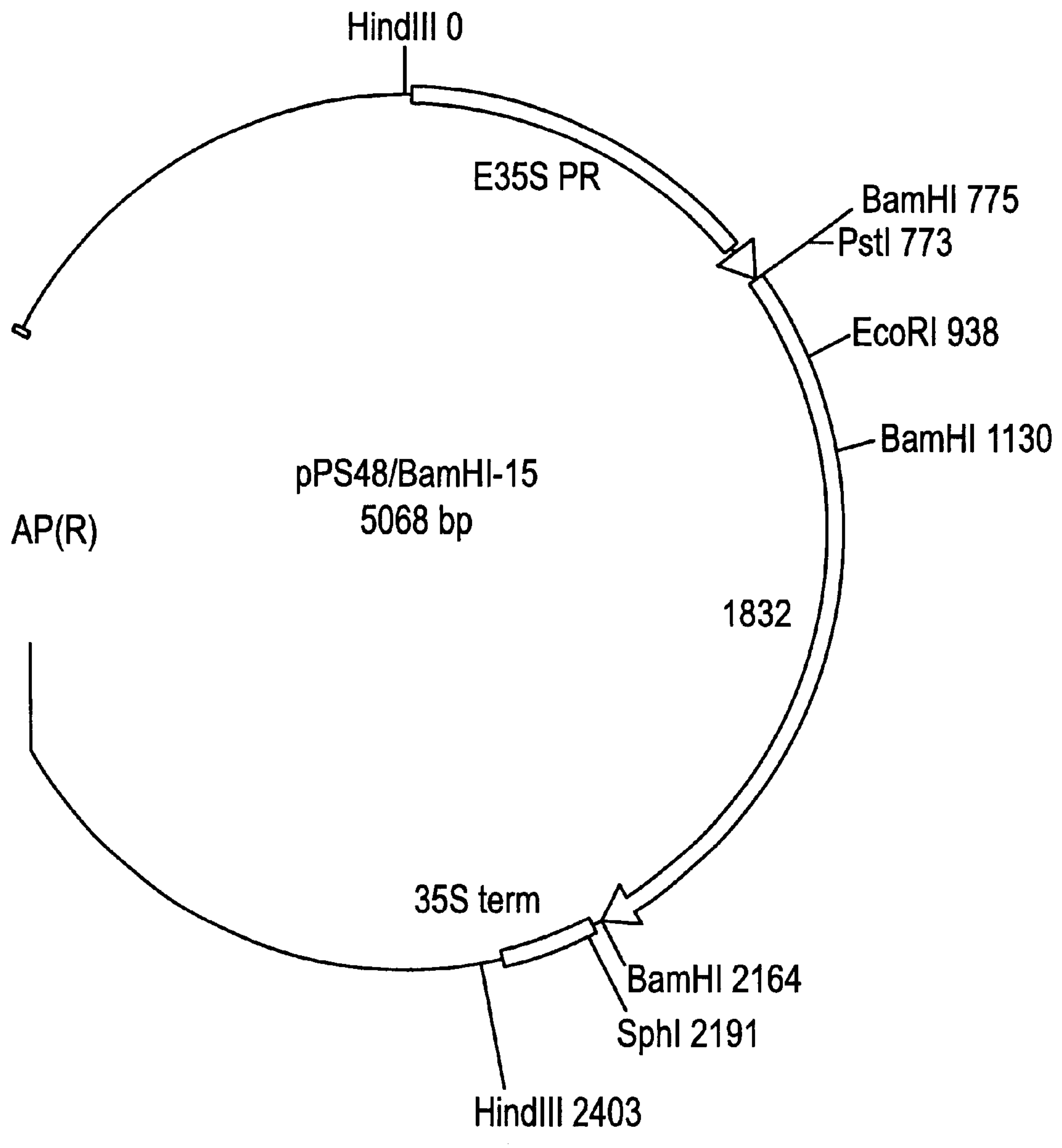

As is shown in FIG. 4, pAM194 includes the following elements:

apart from the boundary sequences (LB; RB), the fragment contains NPTII as a selection marker;

the left and right boundary sequences (LB; RB);

the NPTII gene from Tn5 for selection in plants;

the GUS gene from *E. coli* with the ST-LS1 intron sequence (Vancanneyt et al. 1990);

the 35S promoter-terminator cassette with singular restriction cleavage sites for the purposes of cloning.

Preparation:

The plasmid pBI121 was cleaved with HindIII/SstI. The cleaved HindIII/SstI-35S-GUS fragment was replaced by a subcloned 35S-GUS intron fragment. The EcoRI restriction cleavage site was destroyed by cleaving with EcoRI and filling the overlapping ends with "Klenow fragment" from *E. coli* polymerase I; next a fresh ligation was performed to produce pBIN-GUSTNT. A 35S-promoter-35S-terminator cassette with a single EcoB cloning site from the plasmid pRT104 (Töpfer et al. 1987) was cloned into the HindIII site of pBIN-GUS-INT, leading to pAM194. The literature references cited above are as follows:

Bevan M, 1984: Binary Agrobacterium vectors for plant transformation. Nucleic Acids Research Vol.12, No.22, 8711.

Jefferson R A, Kavanaugh T A, Bevan M W, 1987. EMBO Journal Vol.6, 3901.

Töpfer R, Matzeit V, Gronenborn B, Schell J, Steinbiss H H, 1987: A set of plant expression vectors for transcriptional and translational fusions. Nucleic Acids Research Vol.15, No.14, 5890.

Vancanneyt G, Schmidt R, O'Connor-Sanches A, Willmitzei L, Rocha-Sosa M, 1990:

Construction of an intron-containing marker gene. Molecular General Genetics, 245–250.

The construction of the plasmid is shown schematically in FIG. 4.

EXAMPLE 12

Transformation of Sugar-Beet

For the transformation, *Agrobacterium tumefaciens*, strain EHA101 (Hood E E et al, 1986, J. Bacteriology 168, pp.1291–1301), which had been transformed with the plasmid LD 10/1832-13 (FIGS. 5*a* to *d*) or with the vector LD10, a plasmid which lacked the 1832 cDNA, by the freeze-thaw procedure (Holters et al., 1978), was used.

For the transformation of the sugar-beet, sterile sugar-beet seeds of the type "Elite O-272" were germinated on a medium containing 2.0 g/l sucrose and 4.0 g/l agarose. The embryos were cut off and the cotyledons were carefully removed and used as explants. The *Agrobacterium tumefaciens* strain EHA101 with the plasmid LD10/1832-13, or the control with plasmid LD10 (FIG. 5*c*) was cultivated on LB medium (Maniatis et al., 1982), to which had been added 50 mg/l kanamycin, 75 mg/l spectinomycin, 150 mg/l streptomycin and 50 mg/l acetosyringon, on a rotary shaker (340 RPM) at 27° C. up to an OD of about 1.0 (at 660 nm). The bacterial suspension was then diluted to OD 0.1 with LB, and used for the inoculation with the explants, which were cocultivated for 2 to 4 days at 22° C.

The selection for transgenic shoots was performed using a modification of the mannose selection system. In this way, transgenic sugar-beet shoots were selected for. After the co-cultivation, the explants were transferred to selection medium consisting of MS-medium (Murashige and Skoog 1962), to which had been added 0.05 mg/l α-naphthylacetic acid, 0.25 mg/ml 6-benzyladenine, 500 mg/l carbenicillin, 20 g/l sucrose and D-mannose, the concentration of D-mannose being increased stepwise during the selection, starting with a concentration of 1.25 g/l for the first two subculture periods, then increasing it to 5.0 g/l for the next 2 subculture periods, and finally increasing the concentration to 10 g/l mannose for the last period. Each subculture period lasted 3 weeks. The mannose-resistant shoots were cultivated further on MS medium to which 0.25 mg/l 6-benzyladenine had been added, and the formation of the roots occurred essentially according to Miedema (1982).

The analysis of the mannose-resistant shoots was then performed as follows. To ensure that the mannose-resistant shoots which survived the selection were of a transgenic nature, all shoots were investigated for PMN activity. The non-transgenic sugar-beet shoots show no PMI (phosphomannose isomerase) activity. Extracts from 2–3 leaf-tips ca 3 mm in size were prepared and subjected to the coupled PMI enzyme assay, modified after Feramisco et al. (1973) and Gill et al. (1986). About 80–90% of the shoots showed significant PMI activity. The remaining 10–20% were discarded.

For the nematode test, the shoots with PMI activity and good root development (4–6 weeks old) were removed from the agar plates, and the roots were carefully washed in tap-water. A hole was made in a 4×2×12 cm sand-column, the sides of which were wrapped in plastic, and the shoots were planted in this. The sand was carefully added around the roots and carefully watered, and the plants in the sand-column were placed under a plastic tent for 10 days at 25° C. From time to time during this period, the tent was removed, in order to harden off the plants. These plants were inoculated with nematodes using a syringe, 200 juvenile (J2) nematodes being introduced into the sand in each case, as close as possible to the individual plants. 3 weeks after the inoculation, the female cysts developed and they were quantitatively estimated using a stereoscopic microscope. The whole root of every single plant was examined. The results obtained are shown in table 1. This table shows the results that were obtained with the non-transgenic susceptible line C1, the transgenic control line CLD10, the non-transgenic susceptible control, which were developed from seeds (C2), and the transgenic plants which contain the construct LD10/1832-13 (T1–T9).

| Plant | Number of plants | Mean number of cysts/plant | ID number |
|---|---|---|---|
| control $C_1$ | 4 | 9 | lab 535 |
| control $C_2$ | 9 | 9.3 | seed plants |
| control CLD10 | 2 | 9.5 | T9600130 |
| $T_1$ | 2 | 14 | 1458D |
| $T_2$ | 2 | 9.5 | 1468A |
| $T_3$ | 2 | 4 | 143614J |
| $T_4$ | 4 | 4.3 | 14479K |
| $T_5$ | 2 | 2.5 | 144710L |
| $T_6$ | 3 | 5.3 | 14054D |
| $T_7$ | 4 | 6.75 | 142611H |
| $T_8$ | 5 | 5 | 14052B |
| $T_9$ | 4 | 7.5 | 14053C |

9 independent transgenic lines with the construct LD10/1832-13 were analysed in this test. 2 ($T_1$ and $T_2$) developed about the same number of cysts as the controls $C_1$, $C_2$ and CLD10. 3 of the transgenic plants ($T_3$, $T_4$ and $T_5$) show cyst development about half that of the controls, indicating that the gene is active to a certain degree in these plants. One of the transgenic lines, $T_5$, shows cyst development that corresponds to the previously reported results (Cai et al., 1997). The $T_5$ line developed an average of only 2.5 cysts per plant, this being markedly lower than the number of cysts which was observed in the average of about 10 plants for the various controls. This clearly shows that the 1832 gene is active in the roots of a sugar-beet line which is of commercial interest.

The literature sources mentioned above are as follows:

Cai D, Kleine M, Kifle S, Harloff H-J, Sandal N N, Marcker K A, Klein-Lankhorst R M, Salentijn E M J, Lange W, Stiekema W J, Wyss U, Grundler M W and Jung C (1997). Science 275, 832–834.

Feramisco R, Tilley B E, Conn W R, Gracy R W, Noltman E A (1973). Biochem. Biophys. Res. Comm. 55, 636–641.

Gill J F, Deretic V, Chakrabarty A M (1986). J. Bacteriol. 167, 611–615.

Holters et al. (1978). Mol. Gen. Genet. 163, 181–187.

Maruiatis T, Fritsch L F, Sambrook J (1982). Molecular Cloning. A laboratory manual. Cold Spring Harbor Laboratory, New York, USA.

Miedema P (1982). Euphytica 31, 635–643.

Murashige T, Skoog F (1962). Plant Physiol. 15, 473–497.

EXAMPLE 13

Preparation of the Plasmid LD10/1832-13

The preparation of the said plasmid is shown in FIGS. 5*a–d*. The XbaI fragment from nucleotide positions 1521–2904 from the SEQ ID No.1 was filled to blunt ends with Klenow enzyme. This fragment was then introduced into the BamHI site of the plasmid pPS48, equipped with blunt ends. This new plasmid, named pPS48/BamHI-15, was then cleaved with HindIII. The HindIII fragment from base pair 0–2403 was introduced into the HindIII site of the plasmid pLD10, so yielding plasmid LD10/1832-13.

EXAMPLE 14

Transformation of *Brassica napus* with the Sequence 1832 for producing Nematode Resistance and Resistance Test The Ti-plasmid pAM194, containing the gene for the nematode resistance (sequence 1832) was used as the transformation vector. The vector is described in more detail in example 11.

Strain C58C1 ATHV Rif, which is derived from the *Agrobacterium tumefaciens* strain EHA10, which carries the helper plasmid pEHA101 without kanamycin resistance, was used as the bacterial strain.

The strain AIMT corresponds to the above-named strain C58C1 ATHV Rif, which contains the plasmid pAM194-1832.

The culturing of the bacteria for the transformation was performed for the AMT culture on LB agar with 50 mg/l kanamycin and 100 mg/l rifampicin and was kept in the refrigerator until use. Two days before the intended transformation, 30 ml LB nutrient medium are inoculated with the appropriate bacterial culture. For the bacterial selection, the liquid medium, like the LB agar, contains 50 mg/l kanamycin and 100 mg/l rifampicin. The bacteria were incubated for 24 hours in the dark at 28° C. on a shaker at 190 RPM. On the second day, 30 ml LB medium without antibiotics are inoculated with 20 ml of the aforesaid bacterial culture obtained after 24 hours and incubated for a further 24 hours under the same conditions.

For the culturing of summer rape in vitro (*Brassica napus* ssp. *oleifera* cv. summer rape), the seeds are sterilised with NaOCl (3% active chlorine) in sterile conical flasks for 10 minutes, and then rinsed 3× with sterile distilled water. The seeds are then spread on MS-N medium containing B5 microelements and vitamins. 10 seeds are spread in one container containing 50 ml nutrient medium. The seeds are incubated for 4 days at ca. 2000 lux and a day/night rhythm of 16 hrs/8 hrs. The culturing temperature is 25° C.

For the transformation with *A. tumefaciens* (cotyledon transformation), the cotyledons of four-day old embryos were separated just above the meristem with a scalpel. For this, both cotyledons are grasped with forceps and simultaneously separated with a straight cut. Immediately after the separation, the petioles of the cotyledons are dipped for 10 secs in the undiluted bacterial suspension (overnight culture). Then the cotyledons are put back onto the culture medium. The coculture of 48 hrs is carried out at 25° C. and in dim light. After the completion of the coculture, the cotyledons are put in containers with 50 ml MSM medium which contains 750 mg/l carbenicillin to kill the bacteria, and cultivated for 7 days at 25° C. and 2000 lux with 16 hr days. After 7 days on MSM with 750 mg/l carbenicillin, the cotyl-edons are transplanted to the same nutrient medium, which at the start also contains 20 mg/l kanamycin for the shoot selection. In later passages, the kanamycin concentration was increased to 25 mg/l. Non-transgenic callus is removed regularly. For the further selection or for detection of transgenicity, the separated shoots are planted on B5 medium containing 50 mg/l kanamycin and 400 mg/l betabactyl. The cotransferred GUS gene allows a further identification of transgenic shoots at the earliest possible time. The rooting of the transgenic shoots takes place on B5 nutrient medium without hormones.

For the molecular biological detection of the gene transfer, a GUS test is performed as the histochemical detection of β-glucuronidase activity. The enzyme cleaves indole from a synthetic substrate, so that GUS-positive leaf fragments become blue. The test procedure is as per Jefferson R A (1987): Assaying chimeric genes in plants: The GUS gene fusion system. Plant Mol. Biol. Rep. 5, 387–405.

A further molecular biological detection of the gene transfer is the NPTII-ELISA test, in which the formation of the enzyme neomycin-phosphotransferase, which imparts kanamycin resistance to the transgenic plant, is qualitatively and quantitatively determined. The test was performed with the NPTII-ELISA kit (Cat. No. 5307-610101) from the firm CP Instruments Co. Ltd.

In order constantly to have available adequate quantities of larvae for the inoculation in resistance tests with *Heterodera schachtii,* the nematodes were multiplied on the host plants mustard ("Albatross" variety, Petersen-Saatzucht) and root tubers. The seeds are [sterilised] in 3% $Ca(OCl)_2$ solution for 10 min and then rinsed 3–4× with sterile distilled water. Next, the seeds dry on sterile filter-paper and are then planted on water-agar containing 8% agar—agar. After 3–4 days on this agar at 25° C. in darkness, the young embryos are transferred to 0.2 concentrated Knoop medium. At this time, the roots should be about 3–4 cm long. Petri dishes of 15 cm diameter, with lugs, in which two embryos are placed opposite one another, are used. After 14 days' growth in the dark at 25° C., the inoculation is performed with 1000 nematode larvae in the L2 stage. After about 4 weeks at 25° C. in the dark, mature cysts have formed, and can now be collected.

When the cysts are harvested, ca. 200 cysts are collected, using spring-steel forceps, in a small sieve, mesh width 50–200 μm, which is standing in a glass funnel filled with zinc chloride solution (3 mM). At the funnel outlet, a silicone hose is fastened, which is clamped with a steel hose-clamp. This apparatus stands in a tall 250 ml beaker, which is covered with aluminium foil.

After 3 days at 25° C. in the incubator, the hatched larvae have collected in the silicone hose before the steel clamp and can be harvested in a sieve of 15 μm mesh width by briefly opening the clamp, the funnel being held with forceps. The larvae are now rinsed 3× with sterile water and then transferred with a Pasteur pipette into a sterile block dish. After a pause of about 3 mins, during which the larvae sink to the bottom, the excess liquid is as far as possible removed by suction, and replaced with 0.5% Gelrite solution, which ensures a homogeneous distribution of the larvae. After careful nixing, the concentration of the larvae is checked using a stereoscopic microscope, the larvae in a 10 μl droplet being counted.

For the in vitro tests, the roots are separated from the shoots of the transgenic starting clone and laid on ½

B5-medium containing 300 mg/l betabactyl and 8 g/l Daishin agar. Each inoculation of a transgenic starting clone is performed with 5 roots. As a susceptible control, oil radish, whose roots were obtained as described above, is used. Per dish, about 100 L2 larvae of *Heterodera schachtii* are dropped onto the roots, which were obtained as described above. For the inoculation, a Multipette with a 0.5 ml Combitip is used. The dishes sealed with Parafilm are incubated at 25° C. in darkness. The first counting of the cysts formed takes place after 14 days, and the second and last counting after 20 days, when the cysts have already become pale brown and hence are more easily lifted off the white roots.

For the in situ tests, 5 shoots for each transgenic starting clone are first transferred to the greenhouse. For this, the shoots should already have extended somewhat and possess a few roots. They are pricked out in potting soil, in which they remain for 1.5 weeks, so as to develop more root mass. In addition, this gives them the opportunity to acclimatise to the greenhouse conditions. After 1.5 weeks, the plants are pricked out in quartz sand with a grain size of 0.1–0.5 cm, which has previously been moistened with nutrient solution after Steiner. The inoculation is performed in this sand, since the cleaning and counting of the cysts is made very difficult by humus particles and dirt particles. The sand is in tubes which are stood in a box. Since the edge regions of a box give the plants more light and hence better growing conditions, the test plants are surrounded by other plants, so that every test plant has a neighbour. One week after the second pricking-out date, the inoculation is performed with (600) freshly hatched *H. schachtii* larvae, L2 stage. The assessment is made after ca. 6 weeks, when the cysts have become brown and can easily be rinsed away from the roots. The cysts are separated from the plant roots by rinsing through a kitchen sieve with a powerful water jet, caught in a 100 um sieve and separated from the sand by centrifugation. The mixture of cysts, fine roots and water obtained is filtered and the cysts are then counted under a binocular microscope at 10×magnification.

The transgenicity of the plants was demonstrated by PCR analyses and NPTII-ELISA and GUS tests.

The table shows the results from the in vivo resistance test with the non-transgenic susceptible variety To and the transgenic plants $T_7$ to $T_{15}$ containing the gene 1832.

| Ident. No. | Number of roots | Mean cysts/root |
|---|---|---|
| $T_7$ | 10 | 14.4 |
| $T_8$ | 9 | 19.0 |
| $T_{81}$ | 2 | 14.5 |
| $T_9$ | 7 | 21.3 |
| $T_{10}$ | 6 | 18.8 |
| $T_{11}$ | 6 | 10.2 |
| $T_{12}$ | 5 | 23.6 |
| $T_{13}$ | 5 | 18.4 |
| $T_{14}$ | 9 | 19.2 |
| $T_{15}$ | 3 | 14.7 |
| $T_0$ | 9 | 19.1 |

10 independent, transgenic lines containing the gene 1832 were assessed in this test. 6 lines ($T_8$, $T_9$, $T_{10}$, $T_{11}$, $T_{13}$ and $T_{14}$) had a comparable number of cysts to the susceptible line; 3 lines ($T_7$, $T_8$, and $T_{15}$) had a 27% reduction in cysts compared to the control and 1 line ($T_{11}$) a 47 % reduction in cysts. This shows that the gene is active in the plants and a marked reduction in cyst infestation is achievable in *Brassica nagus.*

EXAMPLE 15

Potatoes of the Bintje variety were transformed with the plasmid pAM194 containing the insert 1832 under the control of the 35S promoter with *A. rhizogenes.* 40 independent hairy root cultures were each inoculated with 250 *Globodera pallida* larvae. After 56 days, the nematode development was investigated. 35 cultures showed normal nematode development with on average 40 mature females/Petri dish. In 5 root cultures, the development of females was disrupted. There only 10 mature females were found in each. This shows that in potatoes the sequence 1832 can improve their resistance against nematode attack.

What is claimed is:

1. An isolated nucleic acid molecule, wherein the nucleic acid molecule encodes a polypeptide that induces a resistance against sedentary nematodes in plants selected from the group of families consisting of Solanaceae, Chenopodiaceae, and Brassicaceae, and wherein the nucleic acid molecule is selected from the group consisting of SEQ ID NO: 1, SEQ ID NO: 2 or a nucleic acid molecule having a sequence identity of at least 60% therewith.

2. The nucleic acid according to claim 1, wherein the plant is selected from the group of genera consisting of Beta, Brassica, and Solanum.

3. The nucleic acid according to claim 1, wherein the $HSI^{pro-1}$ gene comprises SEQ ID NO:2.

4. The nucleic acid molecule according to claim 1, wherein the nucleic acid is obtainable by screening a DNA library with a DNA molecule comprising the sequence of SEQ ID NO:2.

5. The nucleic acid molecule according co claim 1, wherein the nucleic acid is DNA.

6. The nucleic acid molecule according to claim 5, wherein the DNA is cDNA.

7. The nucleic acid molecule according to claim 1, wherein the nucleic acid molecule is derived from a wild species of the section Procumbentes of the genus Beta.

8. The nucleic acid molecule according to claim 1, wherein the nucleic acid molecule induces a resistance against sedentary nematodes selected from the group of genera consisting of Meloidogyne, Heterodera, and Globodera.

9. The nucleic acid molecule according to claim 1, wherein the nucleic acid molecule induces a resistance against *Heterodera schachtii.*

10. The nucleic acid molecule according to claim 1, wherein the nucleic acid molecule induces a resistance against sedentary nematodes in plants of the species *Beta vulgaris.*

11. A vector, comprising the nucleic acid molecule according to claim 1.

12. The vector according to claim 11, wherein the vector is a YAC vector.

13. A method for inducing resistance in a plant against sedentary nematodes, comprising growing a transgenic plant comprising the vector of claim 11 under conditions such that said plant produces a polypeptide that induces a resistance against said sedentary nematodes.

14. A transgenic plant, comprising the vector according to claim 11.

15. The transgenic plant according to claim 14, wherein the plant is selected from the group of plant genera consisting of Beta and Brassica.

16. The transgenic plant according to claim 15, wherein the plant is *Beta vulgaris.*

17. A transgenic cell, seed or plant part, each comprising the vector according to claim 11.

18. A method for inducing a resistance in a plant against sedentary nematodes, comprising growing a transgenic plant comprising the nucleic acid molecule of claim 1 under conditions such that said plant produces a polypeptide that induces a resistance against said sedentary nematodes.

19. A transgenic plant, comprising the nucleic acid molecule according to claim 1.

20. The transgenic plant according to claim 19, wherein the plant is selected from the group of genera consisting of Beta and Brassica.

21. The transgenic plant according to claim 20, wherein the plant is *Beta vulgaris.*

22. A transgenic cell, seed or plant part, each comprising the nucleic acid molecule according to claim 1.

23. A process for producing a plant, comprising introducing the nucleic acid molecule according to claim 1 into a plant cell, and regenerating a plant from the plant cell.

24. An isolated nucleic acid that specifically hybridizes under highly stringent conditions to the complement of the sequence set forth in SEQ ID NO: 2, wherein said nucleic acid encodes a protein that induces a resistance against sedentary nematodes in plants selected from the group of families consisting of Solanaceae, Chenopodiaceae, and Brassicaceae.

* * * * *